(12) United States Patent  
Kondo et al.

(10) Patent No.: US 8,539,817 B2  
(45) Date of Patent: Sep. 24, 2013

(54) PARTICULATE MATTER DETECTION DEVICE

(75) Inventors: Atsuo Kondo, Nagoya (JP); Takeshi Sakuma, Nagoya (JP); Masahiro Tokuda, Nagoya (JP); Takashi Egami, Nagoya (JP); Keizo Iwama, Wako (JP); Masanobu Miki, Wako (JP)

(73) Assignees: NGK Insulators, Ltd., Nagoya (JP); Honda Motor Co., Ltd., Minato-Ku (JP)

( * ) Notice: Subject to any disclaimer, the term of this patent is extended or adjusted under 35 U.S.C. 154(b) by 218 days.

(21) Appl. No.: 13/221,979

(22) Filed: Aug. 31, 2011

(65) Prior Publication Data

US 2012/0055233 A1   Mar. 8, 2012

(30) Foreign Application Priority Data

Sep. 7, 2010 (JP) ................................. 2010-199914

(51) Int. Cl.  
*G01N 37/00* (2006.01)

(52) U.S. Cl.  
USPC .......................................................... 73/28.02

(58) Field of Classification Search  
USPC ................. 73/28.01, 28.02, 863.21  
See application file for complete search history.

(56) References Cited

U.S. PATENT DOCUMENTS

| 7,041,153 B2* | 5/2006 | Totoki ................................. 95/3 |
| 2010/0000863 A1 | 1/2010 | Kondo et al. |
| 2010/0071441 A1* | 3/2010 | Sakuma et al. ............... 73/28.01 |
| 2010/0313761 A1* | 12/2010 | Tanaka et al. ..................... 96/52 |

FOREIGN PATENT DOCUMENTS

| JP | 2009-186278 A1 | 8/2009 |
| JP | 2010-032488 A1 | 2/2010 |

* cited by examiner

*Primary Examiner* — Hezron E Williams  
*Assistant Examiner* — David Z Huang  
(74) *Attorney, Agent, or Firm* — Burr & Brown

(57) ABSTRACT

A particulate matter detection device includes a plate-like element base material including, on one surface thereof, a formed recess portion to collect a particulate matter; a pair of measurement electrodes arranged on the bottom surface side of the recess portion of the element base material; and a high-voltage dust collection electrode embedded in a wall which forms the recess portion of the element base material on the one surface side of the element base material from a position where the pair of measurement electrodes are arranged. An electric field is generated from the high-voltage dust collection electrode to the pair of measurement electrodes, to collect, on the bottom surface side of the recess portion, the particulate matter flowing along the element base material, and a change of electric characteristics between the pair of measurement electrodes is measured to detect the particulate matter collected on the recess portion.

12 Claims, 13 Drawing Sheets

PARTICULATE MATTER DETECTION DEVICE

BACKGROUND OF THE INVENTION

1. Field of the Invention

The present invention relates to a particulate matter detection device, and more particularly, it relates to a particulate matter detection device having a simple constitution and capable of accurately detecting a particulate matter.

2. Description of the Related Art

A flue exhaust gas and a diesel engine exhaust gas include a particulate matter (PM) such as soot, which has been a cause for air pollution. For the purpose of removing the particulate matter, a filter (a diesel particulate filter: DPF) made of a ceramic material and the like have widely been used. The DPF made of the ceramic material can be used for a long period of time, but defects such as cracks and melting damages due to thermal deterioration and the like might be generated, and the particulate matter might leak, although an amount thereof is a micro amount. When such defects are generated, from the viewpoint of the prevention of the air pollution, it is remarkably important to immediately detect the generation of the defects and to recognize the abnormality of a device.

As a method of detecting the generation of such defects, there has been suggested a method of disposing a particulate matter detection device on a downstream side of the DPF (see e.g. Patent Documents 1 and 2).

For example, the particulate matter detection device disclosed in Patent Document 1 includes a detection device main body which has a through hole formed in one end thereof and which is long in one direction, and at least a pair of electrodes embedded in a wall which forms this through hole and covered with a dielectric material. It is possible to electrically adsorb, by the wall surface of this through hole, a charged particulate matter included in a fluid flowing into the through hole, or a particulate matter charged by discharge which occurs in the through hole when a voltage is applied across the pair of electrodes, and included in the fluid flowing into the through hole. When a change of electric characteristics of the wall which forms the through hole is measured, it is possible to detect a mass of the particulate matter adsorbed by the wall surface of the through hole.

Consequently, the conventional particulate matter detection device allows the particulate matter included in a measurement target gas to adhere to and around the pair of electrodes which are sensors, and measures the change of the electric characteristics between the pair of electrodes, to detect the particulate matter in the measurement target gas.

[Patent Document 1] JP-A-2009-186278
[Patent Document 2] JP-A-2010-32488

SUMMARY OF THE INVENTION

The particulate matter detection devices disclosed in Patent Documents 1 and 2 can accurately detect a mass of a particulate matter, but a constitution of each of the devices, especially a constitution of a detection device main body is complicated, which has caused a problem that manufacturing cost increases.

Moreover, a through hole is formed in one end of the detection device main body, and the presence of this through hole also causes a problem that the detection device main body is easily distorted.

Furthermore, when the particulate matter is allowed to adhere to a periphery of the through hole and measured, it is necessary to periodically remove the adhering particulate matter and to regenerate the device. However, for heating the whole wall that forms the through hole, a plurality of heating means such as heaters have to be arranged, whereby the constitution of the device further becomes complicated. Moreover, such heaters have an influence on a measured value sometimes, and hence the number of the heaters is preferably as small as possible.

The present invention has been developed in view of the above problems, and an object thereof is to provide a particulate matter detection device which has a simple constitution and which can accurately detect a particulate matter.

The present inventors have, intensively performed investigations for solving the above problems of the conventional technology, and have found that when a recess portion to collect a particulate matter is formed in one surface of an element base material, a pair of measurement electrodes are arranged on the bottom surface side of the recess portion and a high-voltage dust collection electrode to collect the particulate matter is disposed in a wall which forms this recess portion, it is possible to realize, with a simple constitution, a measurement accuracy which is similar to that of a conventional particulate matter detection device, whereby the present inventors have completed the present invention. Specifically, according to the present invention, the following particulate matter detection device is provided.

[1] A particulate matter detection device comprising: a plate-like element base material including, on one surface thereof, a formed recess portion to collect a particulate matter; a pair of measurement electrodes arranged in a bottom surface of the recess portion of the element base material or in the element base material on the bottom surface side of the recess portion; and a high-voltage dust collection electrode embedded in a wall which forms the recess portion of the element base material at the same height position as a position where the pair of measurement electrodes are arranged in a depth direction of the recess portion or on the one surface side position of the element base material from the position where the pair of measurement electrodes are arranged, wherein an electric field is generated from the high-voltage dust collection electrode to the pair of measurement electrodes arranged in the bottom surface of the recess portion or in the element base material on the bottom surface side of the recess portion, to collect, on the bottom surface side of the recess portion, the particulate matter included in a measurement target gas flowing along the element base material, and a change of electric characteristics between the pair of measurement electrodes is measured to detect the particulate matter collected on the bottom surface side of the recess portion.

[2] The particulate matter detection device according to the above [1], wherein the high-voltage dust collection electrode is disposed to surround the periphery of the recess portion excluding a wall thereof positioned on an inflow side of the measurement target gas.

[3] The particulate matter detection device according to the above [1], wherein the high-voltage dust collection electrode is disposed to surround the whole region around the recess portion.

[4] The particulate matter detection device according to any one of the above [1] to [3], wherein the measurement electrodes constituting the pair of measurement electrodes are combteeth-like electrodes each including a plurality of planarly arranged combteeth portions, and a comb spine portion which connects the plurality of combteeth portions of each of the measurement electrodes to one another at ends thereof, the combteeth portions of the measurement electrodes are arranged to engage with each other via a space, and the pair of measurement electrodes have a constitution in which at least a portion where the plurality of combteeth portions engage with each other is disposed in a region of the bottom surface of the recess portion and in which the comb spine portion of each of the measurement electrodes is disposed in the wall forming the recess portion outside the bottom surface region of the recess portion.

[5] The particulate matter detection device according to any one of the above [1] to [4], further comprising: an earth dust collection electrode for earthing disposed on the surface side of the element base material opposite to the one surface thereof from the position where the pair of measurement electrodes are arranged.

In the particulate matter detection device of the invention according to claim 1, the recess portion to collect the particulate matter is formed in the one surface of the element base material, and the pair of measurement electrodes is arranged on the bottom surface side of the recess portion. Furthermore, the high-voltage dust collection electrode to collect the particulate matter is disposed in the wall which forms this recess portion. In consequence, when a high voltage is applied to the high-voltage dust collection electrode, the electric field can be generated so that an electric force line becomes substantially vertical to the bottom surface of the recess portion. For example, it is possible to detect the particulate matter with about the same accuracy as that of a conventional particulate matter detection device including a through hole formed in one end of a detection device main body thereof.

Moreover, as compared with the above conventional particulate matter detection device, a constitution of the detection device, especially the element base material (corresponding to the detection device main body of the conventional particulate matter detection device) is remarkably simple, and hence manufacturing cost can be decreased. Moreover, the element base material is not easily distorted. Furthermore, regeneration of the device in which the particulate matter adhering to the device is removed can remarkably easily be conducted.

In the particulate matter detection device according to claim 2 of the present invention, the high-voltage dust collection electrode is not disposed in the wall thereof which forms the recess portion on the inflow side of the measurement target gas. Therefore, the flow of the measurement target gas can effectively be prevented from being disturbed by the electric field generated by the high-voltage dust collection electrode, and the particulate matter included in the measurement target gas can satisfactorily be collected on the bottom surface side of the recess portion.

On the other hand, in the particulate matter detection device according to claim 3 of the present invention, the high-voltage dust collection electrode is disposed to surround the whole periphery of the recess portion. Therefore, a uniform electric field can be generated in the recess portion.

In the particulate matter detection device according to claim 4 of the present invention, as the pair of measurement electrodes, a pair of measurement electrodes formed into a combteeth-like shape are used. Therefore, in addition to the effect of the invention according to claim 1, a sensitivity of the detection device can further be enhanced. That is, when such combteeth-like electrodes are used, a space between the electrodes can more uniformly be narrowed. Furthermore, the comb spine portion of at least one of the measurement electrodes is disposed in the wall which forms the recess portion, whereby the comb spine portion of the measurement electrode is excluded from the substantial detection surface, and the particulate matter can satisfactorily be detected. When the combteeth-like electrodes are used as described above, a space between combteeth can uniformly be provided, and a measurement sensitivity can be enhanced. However, a space between portions where the combteeth portions engage with the comb spine portion is different from the space between the combteeth portions. Therefore, the measurement accuracy of the detection device is relatively lowered sometimes owing to the comb spine portion (more specifically, a space between the comb spine portion and the combteeth portion). In the particulate matter detection device according to claim 4 of the present invention, the comb spine portion which becomes such a factor to lower the measurement accuracy is covered with the wall which forms the recess portion, and loses a function of a measurement portion. Therefore, any measured value is not adversely affected by this comb spine portion. That is, the particulate matter can more accurately be detected. Moreover, when the comb spine portion is covered in this manner, an initial value of electric characteristics measured by the pair of measurement electrodes (e.g. a value of an electrostatic capacity in a state where any particulate matter does not adhere) increases. Therefore, the device is remarkably effective, for example, when on-board diagnosis (OBD) of the device is performed by using this initial value.

The particulate matter detection device according to claim 5 of the present invention further comprises the earth dust collection electrode for earthing, whereby the particulate matter can be detected in a more electrically stable state. That is, in the present invention, at least one measurement electrode of the pair of measurement electrodes can be used as an earth electrode (an earth) of the high-voltage dust collection electrode. However, since the device further comprises the above earth dust collection electrode, the detection device can satisfactorily be earthed.

DESCRIPTION OF THE PREFERRED EMBODIMENTS

Hereinafter, modes for carrying out the present invention will specifically be described, but it should be understood that the present invention is not limited to the following embodiments and changes, modifications and the like of design can appropriately be added thereto on the basis of the ordinary knowledge of a person skilled in the art without departing from the scope of the present invention.

Figure 1A:
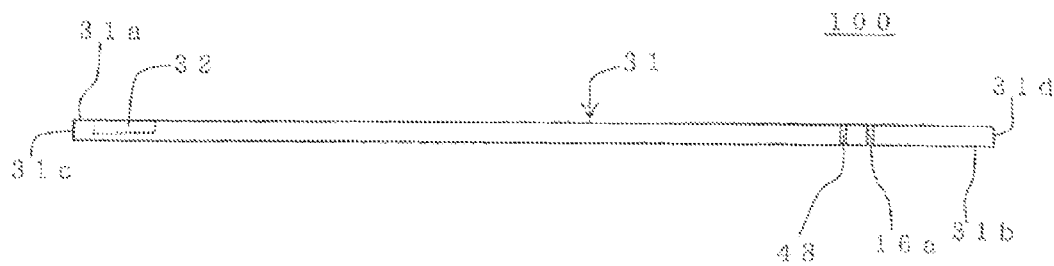
FIG. 1A is a front view schematically showing an embodiment of a particulate matter detection device of the present invention.
Figure 1B:
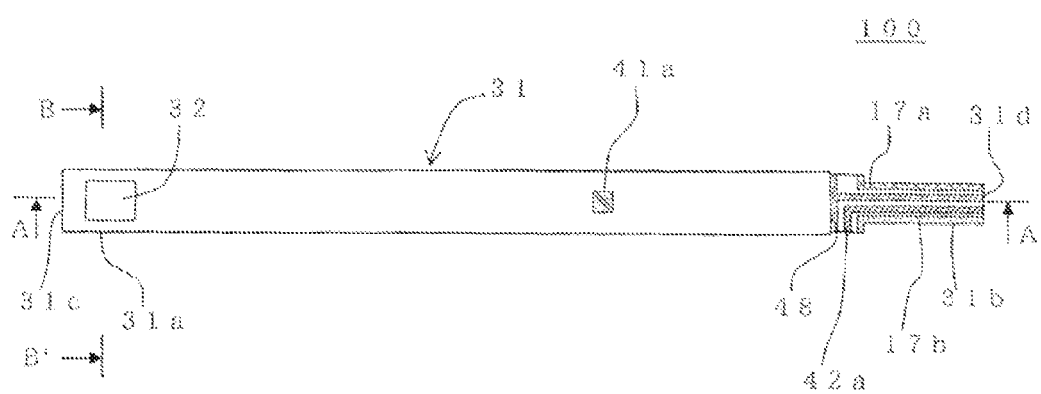
FIG. 1B is a side view showing one side surface of the particulate matter detection device shown in FIG. 1A.
Figure 1C:
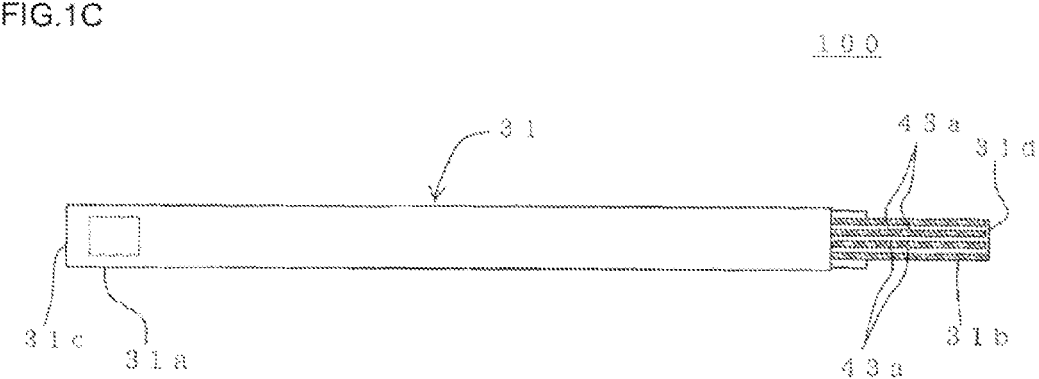
FIG. 1C is a side view showing the other side surface of the particulate matter detection device shown in FIG. 1A.
Figure 1D:
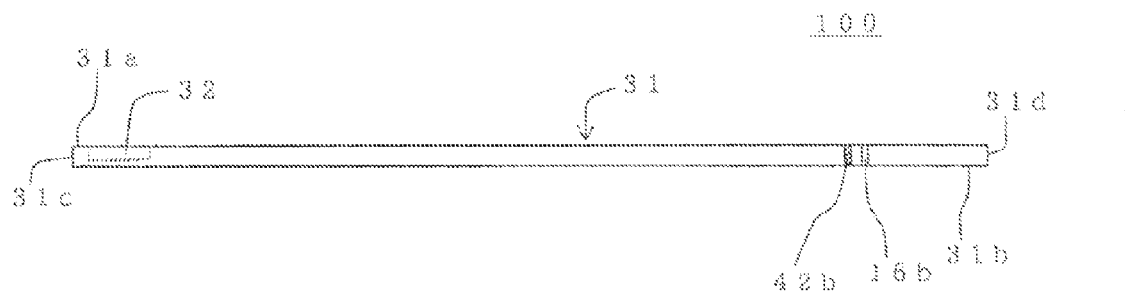
FIG. 1D is a back view of the particulate matter detection device shown in FIG. 1A.
Figure 2:
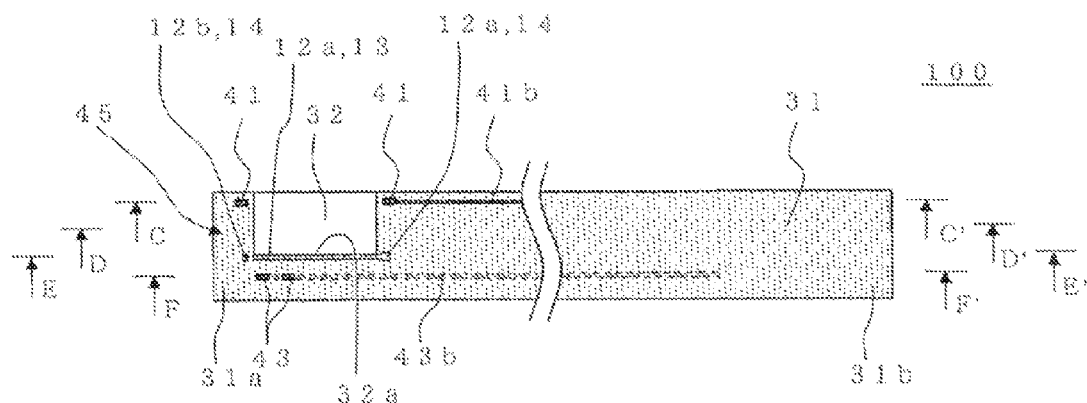
FIG. 2 is a schematic diagram showing a section cut along the A-A' line of FIG. 1B.

[1] Particulate Matter Detection Device:

An embodiment of a particulate matter detection device of the present invention is a particulate matter detection device 100 including a plate-like element base material 31 including, on one surface thereof, a formed recess portion 32 to collect a particulate matter as shown in FIG. 1A to FIG. 1D; a pair of measurement electrodes 12 (12a and 12b) arranged in a bottom surface 32a of the recess portion 32 of the element base material 31 or in the element base material 31 on the bottom surface 32a side of the recess portion 32 as shown in FIG. 2 to FIG. 7; and a high-voltage dust collection electrode 41 embedded in a wall 45 which forms the recess portion 32 of the element base material 31 at the same height position as a position where the pair of measurement electrodes 12a and 12b are arranged in a depth direction of the recess portion 32 or on the one surface side position of the element base material from the position where the pair of measurement electrodes 12a and 12b are arranged (i.e. on the surface side on an opening side of the recess portion 32). It is to be noted that hereinafter "a case where the pair of measurement electrodes are arranged in the bottom surface of the recess portion of the element base material" and "the case where the pair of measurement electrodes are arranged in the element base material on the bottom surface side of the recess portion" are included in "a case where the pair of measurement electrodes are arranged on the bottom surface side of the recess portion" referred sometimes. Moreover, FIG. 2 shows an example of the case where the high-voltage dust collection electrode 41 is disposed in the wall 45 on the one surface side thereof from the position where the pair of measurement electrodes 12a and 12b are arranged.

Figure 3:
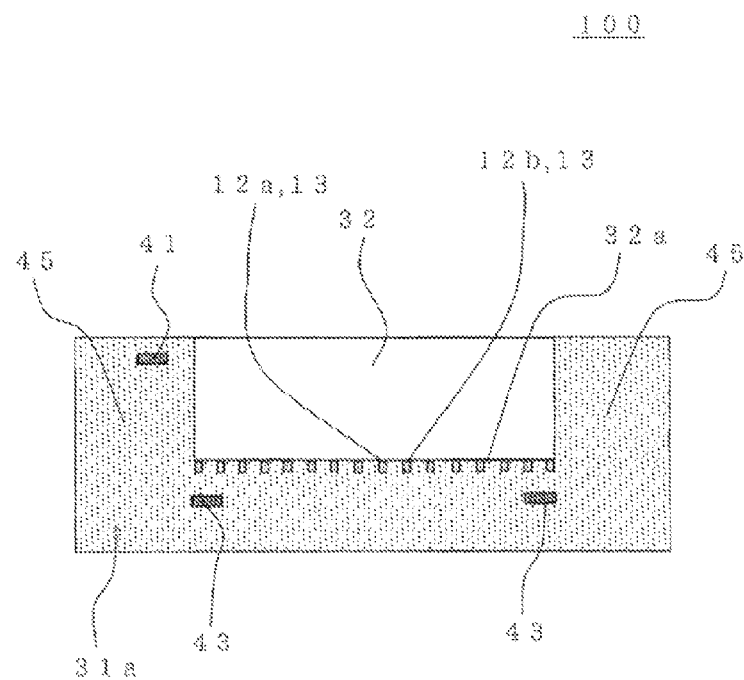
FIG. 3 is a schematic diagram showing a section cut along the B-B' line of FIG. 1B.
Figure 4:
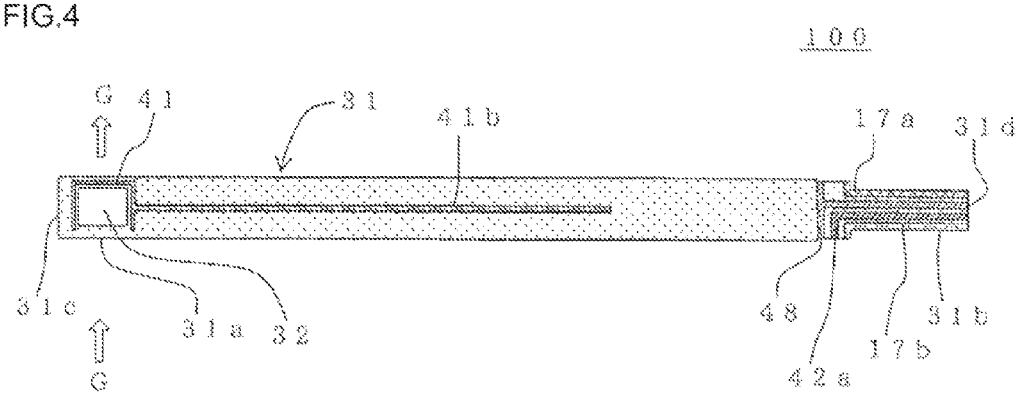
FIG. 4 is a schematic diagram showing a section cut along the C-C' line of FIG. 2.
Figure 5:
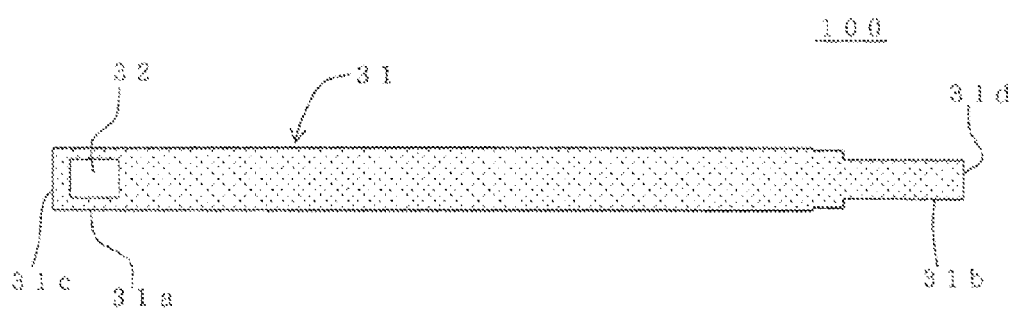
FIG. 5 is a schematic diagram showing a section cut along the D-D' line of FIG. 2.
Figure 6:
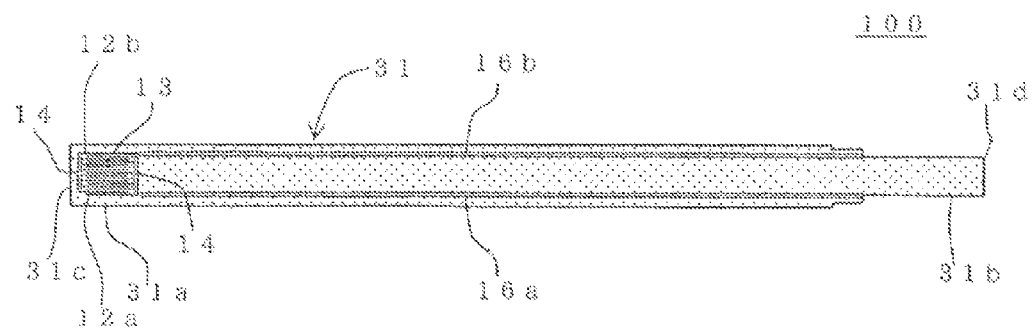
FIG. 6 is a schematic diagram showing a section cut along the E-E' line of FIG. 2.
Figure 7:
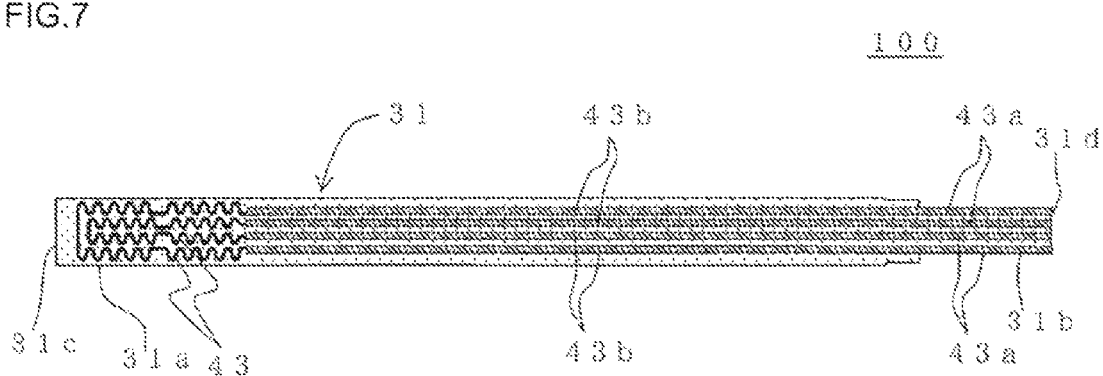
FIG. 7 is a schematic diagram showing a section cut along the F-F' line of FIG. 2.

Here, FIG. 1A is a front view schematically showing the embodiment of the particulate matter detection device of the present invention, FIG. 1B is a side view showing one side surface of the particulate matter detection device shown in FIG. 1A, FIG. 1C is a side view showing the other side surface of the particulate matter detection device shown in FIG. 1A, and FIG. 1D is a back view of the particulate matter detection device shown in FIG. 1A. Moreover, FIG. 2 is a schematic diagram showing a section cut along the A-A' line of FIG. 1B, and FIG. 3 is a schematic diagram showing a section cut along the B-B' line of FIG. 1B. Furthermore, FIG. 4 is a schematic diagram showing a section cut along the C-C' line of FIG. 2, FIG. 5 is a schematic diagram showing a section cut along the D-D' line of FIG. 2, FIG. 6 is a schematic diagram showing a section cut along the E-E' line of FIG. 2, and FIG. 7 is a schematic diagram showing a section cut along the F-F' line of FIG. 2.

Figure 8:
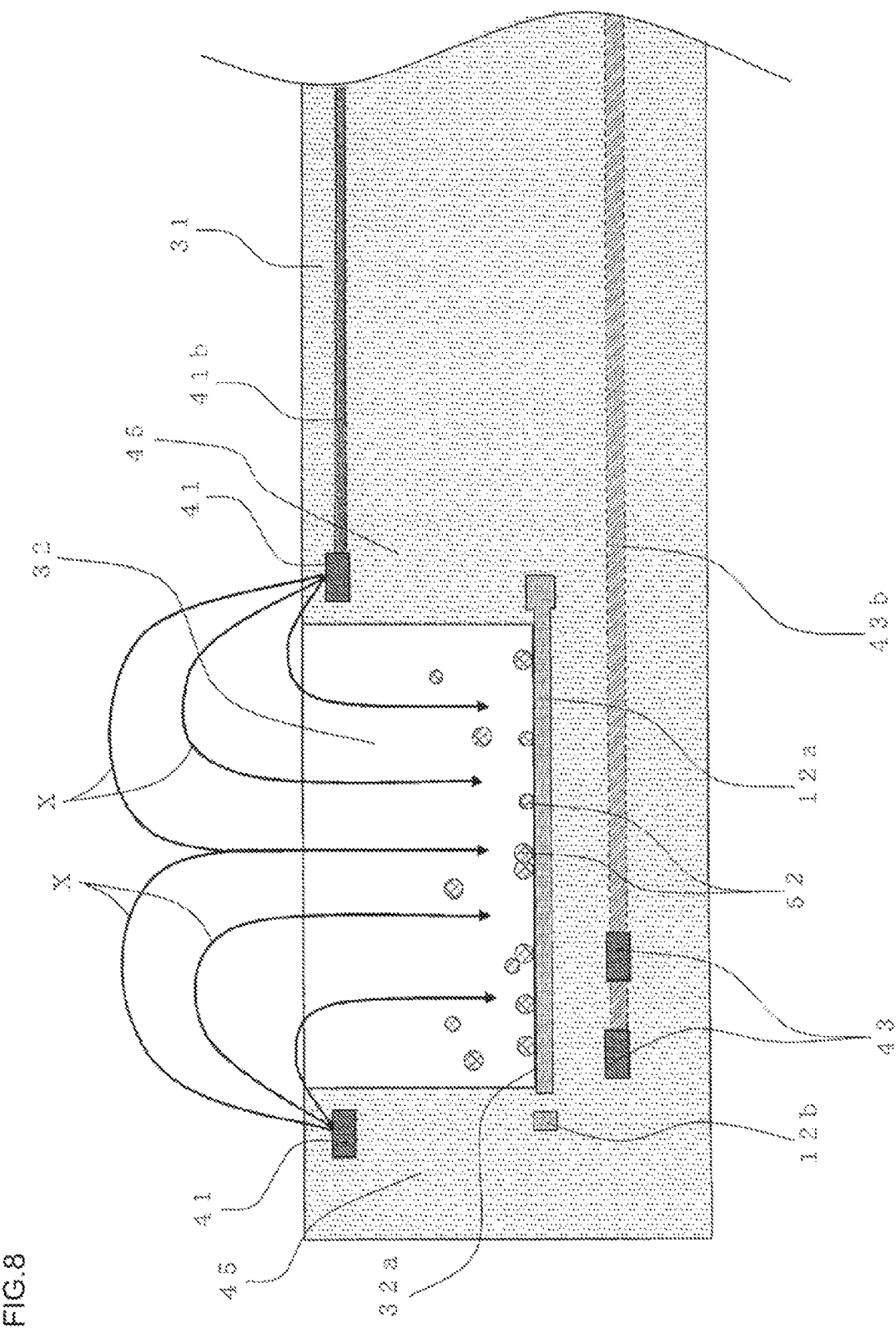
FIG. 8 is an enlarged view schematically showing a state where a high voltage is applied to a high-voltage dust collection electrode in the particulate matter detection device shown in FIG. 2.

Moreover, in the particulate matter detection device 100 of the present embodiment, as shown in FIG. 8, an electric field is generated from the high-voltage dust collection electrode 41 to "the pair of measurement electrodes 12a and 12b arranged in the bottom surface 32a of the recess portion 32 or in the element base material 31 on the bottom surface 32a side of the recess portion 32", to collect, on the bottom surface 32a side of the recess portion 32, a particulate matter 52 included in a measurement target gas flowing along the element base material 31, thereby measuring a change of electric characteristics between the pair of measurement electrodes 12a and 12b to detect the particulate matter 52 collected on the bottom surface 32a side of the recess portion 32.

In particular, as described above, the pair of measurement electrodes 12a and 12b are arranged on the bottom surface 32a side of the recess portion 32, and further in the wall 45 which forms the recess portion 32, the high-voltage dust collection electrode 41 is disposed to collect the particulate matter 52. Even in this case, when the high voltage is applied to the high-voltage dust collection electrode 41 as shown in FIG. 8, the electric field can be generated so that an electric force line is substantially vertical to the pair of measurement electrodes 12a and 12b (in other words, the bottom surface 32a of the recess portion 32), and hence the particulate matter 52 included in the measurement target gas flowing along the element base material 31 can satisfactorily be collected (i.e. captured) on the bottom surface 32a side of the recess portion 32. Here, FIG. 8 is an enlarged view schematically showing a state where the high voltage is applied to the high-voltage dust collection electrode in the particulate matter detection device shown in FIG. 2. It is to be noted that in FIG. 8, the electric force line of the generated electric field is denoted with reference mark X.

Moreover, in the particulate matter detection device 100 of the present embodiment, a constitution of the detection device, especially the element base material (corresponding to e.g. the detection device main body of the particulate matter detection device disclosed in Patent Document 2) is remarkably simple, and hence manufacturing cost can be decreased, as compared with the conventional particulate matter detection device. Moreover, the element base material is not easily distorted. Furthermore, regeneration of the device in which the particulate matter adhering to the device is removed can remarkably easily be conducted.

It is to be noted that in the particulate matter detection device of the present embodiment, a shape of the recess portion, a position of the high-voltage dust collection electrode in the wall which forms the recess portion or the like is appropriately determined so that the particulate matter which is present in the electric field can positively be collected on the bottom surface of the recess portion by the influence of the electric field, when the electric field is generated from the high-voltage dust collection electrode to the pair of measurement electrodes. That is, in the particulate matter detection device of the present embodiment, "the electric field can be generated so that the electric force line becomes substantially vertical to the bottom surface of the recess portion", but when "the electric force line is substantially vertical to the bottom surface of the recess portion" as described above, an angle formed between the electric force line and the bottom surface of the recess portion is such a degree of angle that enables the collection of the particulate matter on the bottom surface of the recess portion by the electric field, and does not have to correctly be 90°. Specifically, for example, an angle which enables the effective collection of the particulate matter on the bottom surface of the particulate matter is from about 75° to 105°.

There is not any special restriction on the electric force line of the electric field generated by the high-voltage dust collection electrode, as long as the electric force line becomes substantially vertical to at least part of the bottom surface of the recess portion. According to such a constitution, it is possible to satisfactorily collect, on the bottom surface side of the recess portion, the particulate matter in the measurement target gas flowing along the element base material, more specifically, the measurement target gas flowing along the element base material and influenced by the electric field generated by the high-voltage dust collection electrode.

"The recess portion" formed in the element base material is a depression which opens in one surface of the plate-like element base material and which is formed by hollowing part of the element base material in a thickness direction of this element base material (i.e. a direction from the one surface of the element base material to the opposite surface thereof). It is to be noted that as to this recess portion, it is necessary to form at least one recess portion in the element base material, and two or more recess portions may be formed.

Such a recess portion forms a space which collects the particulate matter included in the measurement target gas, to collect the particulate matter on the bottom surface of the recess portion. Moreover, the pair of measurement electrodes for measuring electric characteristics which change with the collected particulate matter are arranged in the bottom surface of the recess portion or in the element base material on the bottom surface side of the recess portion. Therefore, the bottom surface of the recess portion is preferably, for example, a flat surface so that the particulate matter is easily collected and the electric characteristics can stably be measured by the pair of measurement electrodes.

There is not any special restriction on characteristics of a shape of the opening of the recess portion. The shape is, for example, a quadrangular shape as shown in FIG. 1A, and may be another shape such as a polygonal shape, a round shape or an elliptic shape. There is not any special restriction on a size of the opening of the recess portion, or a depth of the recess portion (i.e. a length of the recess portion in a thickness direction of the element base material), and the size or the depth can appropriately be determined in accordance with a size of the whole detection device, a size of the pair of measurement electrodes arranged in the bottom surface of the recess portion, an intensity of the electric field generated by the high-voltage dust collection electrode or the like.

"The wall which forms the recess portion", in which the high-voltage dust collection electrode is disposed, is the element base material which constitutes the side surface of the recess portion. Moreover, "the wall which forms the recess portion" is the one surface side of the element base material from the position where the pair of measurement electrodes are arranged, and the element base material which constitutes the periphery of the side surface of the recess portion.

The high-voltage dust collection electrode which generates the electric field to collect the particulate matter is embedded in the wall which forms the recess portion. When the high voltage is applied to the high-voltage dust collection electrode, in the particulate matter detection device 100 shown in FIG. 2 to FIG. 7, the pair of measurement electrodes 12a and 12b become earths. The electric field can be generated toward the pair of measurement electrodes 12a and 12b, i.e., the bottom surface 32a of the recess portion 32 in which the pair of measurement electrodes 12a and 12b are arranged.

The high-voltage dust collection electrode may be disposed in at least part of the wall which forms the periphery of the recess portion. For example, as shown in FIG. 2 and FIG. 4, the high-voltage dust collection electrode 41 may be disposed to surround the periphery of the recess portion excluding the wall positioned on the inflow side of the measurement target gas. That is, FIG. 4 shows that a flow direction of the measurement target gas is shown by arrows denoted with mark G and shows a case where in one-side wall on the inflow side of the measurement target gas around the recess portion 32 having the opening with a rectangular shape, the high-voltage dust collection electrode 41 is not disposed, and along the remaining three sides, the high-voltage dust collection electrode 41 is disposed in a U-shape.

According to such a constitution, the flow of the measurement target gas can effectively be prevented from being disturbed by the electric field generated by the high-voltage dust collection electrode, and the particulate matter included in the measurement target gas can satisfactorily be collected on the bottom surface side of the recess portion.

Figure 9:
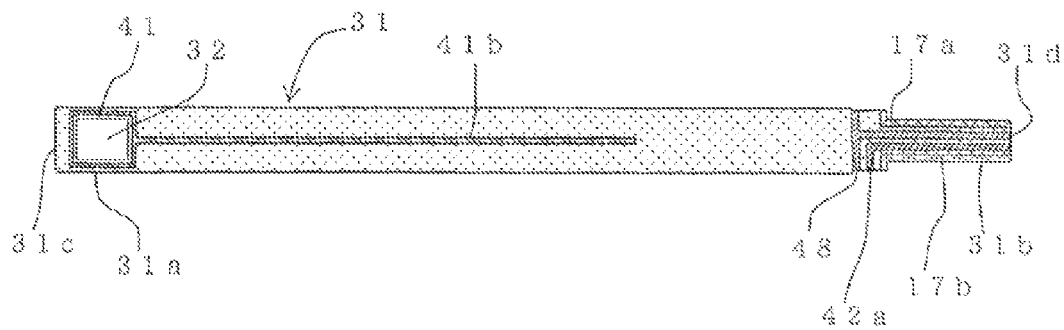
FIG. 9 is a schematic diagram showing a section which is similar to the section cut along the C-C' line of FIG. 2, in another embodiment of the particulate matter detection device of the present invention.
Figure 10:
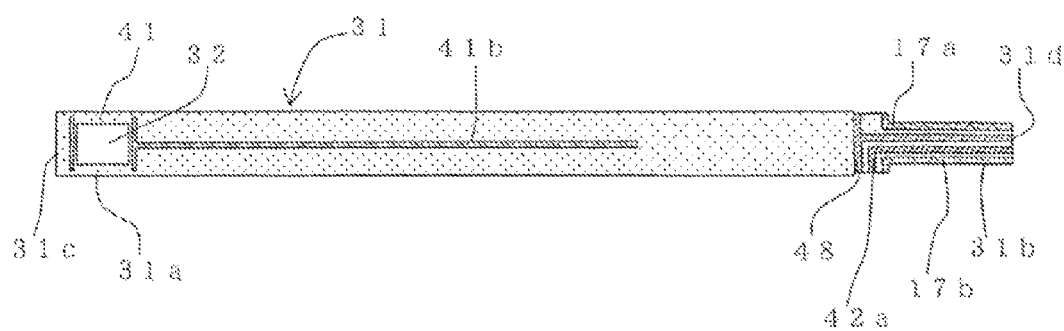
FIG. 10 is a schematic diagram showing a section which is similar to the section cut along the C-C' line of FIG. 2, in still another embodiment of the particulate matter detection device of the present invention.

It is to be noted that as in, for example, a particulate matter detection device 101 shown in FIG. 9, a high-voltage dust collection electrode 41 may be disposed to surround the whole region around a recess portion 32, or as in a particulate matter detection device 102 shown in FIG. 10, high-voltage dust collection electrodes 41 may be arranged along two facing sides around the recess portion 32 having an opening with a rectangular shape. Here, each of FIG. 9 and FIG. 10 is a schematic diagram showing a section which is similar to the section cut along the C-C' line of FIG. 2, in another embodiment of the particulate matter detection device of the present invention.

When the high-voltage dust collection electrode 41 is disposed to surround the whole region around the recess portion 32, a uniform electric field can be generated in the recess portion 32. It is to be noted that in the particulate matter detection device of the present embodiment, the high-voltage dust collection electrodes are preferably arranged along at least two facing sides (two portions) around the recess portion as shown in FIG. 10. According to the above constitutions, the electric field for collecting the particulate matter can satisfactorily be generated. It is to be noted that when the high-voltage dust collection electrodes are arranged along the two facing sides around the recess portion, the above high-voltage dust collection electrodes are more preferably arranged along two facing sides which are parallel to the flow direction of the measurement target gas, around the recess portion.

Moreover, as shown in FIG. 9 and FIG. 10, the high-voltage dust collection electrode 41 may be disposed in the whole side edge region from the inflow side to an outflow side in the flow direction of the measurement target gas around the recess portion 32 (i.e. the whole region (the whole side edge region) of the recess portion 32 in the width direction of the element base material), but the high-voltage dust collection electrode may partially be disposed, for example, on part of the inflow side or part of the outflow side around the recess portion 32.

That is, when the high-voltage dust collection electrode 41 is disposed in the whole side edge region of the opening 32, an electric field having a uniform intensity can be generated from the inflow side to the outflow side in the flow direction of the measurement target gas. On the other hand, when the high-voltage dust collection electrode is disposed on part of the inflow side or on part of the outflow side, the intensity of the electric field can be varied in the flow direction of the measurement target gas in the recess portion. For example, when the high-voltage dust collection electrode is disposed on part of the inflow side, the electric field on the inflow side becomes intense. In an initial measurement step, the particulate matter can satisfactorily be detected on the inflow side. Moreover, when a large amount of the particulate matter adheres to the bottom surface of the recess portion on the inflow side and a measurement sensitivity cannot easily be obtained, it is possible to continuously measure the particulate matter in the bottom surface of the recess portion on the outflow side.

Hereinafter, the particulate matter detection device of the present embodiment will be described in more detail with respect to the particulate matter detection device 100 shown in FIG. 1A to FIG. 7.

[2] Constitution of Particulate Matter Detection Device:

A particulate matter detection device 100 of the present embodiment includes a plate-like element base material 31 including, on one surface thereof, a formed recess portion 32 to collect a particulate matter; a pair of measurement electrodes 12 (12a and 12b) arranged in a bottom surface 32a of the recess portion 32 of the element base material 31 or in the element base material 31 on the bottom surface 32a side of the recess portion 32 as shown in FIG. 2 to FIG. 7; and a high-voltage dust collection electrode 41 disposed in a wall 45 which forms the recess portion 32 of the element base material 31 on the one surface side of the element base material (i.e. the surface side on which the recess portion 32 opens) from a position where the pair of measurement electrodes 12a and 12b are arranged. In the particulate matter detection device 100, an electric field is generated by the dust collection electrode 41, whereby the particulate matter included in a measurement target gas is collected on the bottom surface 32a side of the recess portion 32, and can be adsorbed by the bottom surface 32a of the recess portion 32. Moreover, the particulate matter detection device 10.0 of the present embodiment further includes a heating portion 43 for burning and removing the particulate matter adsorbed by the bottom surface 32a of the recess portion 32.

[2-1] Element Base Material:

The element base material is a portion which becomes a base of the particulate matter detection device including the formed recess portion 32 for collecting the particulate matter on the one surface thereof. The element base material is made of a dielectric material, and the high-voltage dust collection electrode is disposed in the wall which forms the recess portion of the element base material.

The element base material is preferably a plate-like material which is long in one direction. Furthermore, in one end of this plate-like element base material which is long in the one direction, the above recess portion is more preferably formed. According to this constitution, when the particulate matter detection device is inserted into an exhaust gas pipe or the like, the particulate matter in an exhaust gas (the measurement target gas) can efficiently be sampled.

The dielectric material constituting the element base material is preferably at least one selected from the group consisting of, for example, alumina, cordierite, mullite, glass, zirconia, magnesia and titania. Among the materials, alumina can preferably be used. When the high-voltage dust collection electrode is embedded in the element base material made of such a dielectric material, it is possible to form the high-voltage dust collection electrode covered with the dielectric material. Moreover, the particulate matter detection device has an excellent heat resistance, a resistance to dielectric breakdown or the like. Here, "the dielectric material" is a substance which is excellent in dielectric properties rather than in conductivity and which behaves as an insulator against a direct-current voltage.

It is to be noted that "the one end of the element base material" is a region from one tip portion 31c of the element base material to a position corresponding to a length which is 50% of the total length of the element base material 31. Moreover, "the other end of the element base material" is a region from the other tip portion 31d of the element base material to a position corresponding to a length which is 50% of the total length of the element base material 31. It is to be noted that the one end of the element base material is preferably a region from the one tip portion 31c of the element base material to a position corresponding to a length which is 40%, and further preferably 30% of the total length of the element base material 31. Moreover, the other end of the element base material is a region from the other tip portion 31d of the element base material to a position corresponding to a length which is preferably 40%, and further preferably 30% of the total length of the element base material 31. A position between the one end 31a and the other end 31b of the element base material 31 is a portion obtained by excluding regions of the one end 31a and the other end 31b from the element base material 31 (see FIG. 1A to FIG. 1D).

Moreover, there is not any special restriction on a thickness of the element base material 31 (i.e. the thickness in a direction from the one surface provided with the opening of the recess portion to the opposite surface), but the thickness can appropriately be determined in consideration of a depth of the recess portion, thicknesses or arrangement positions of the Pair of measurement electrodes arranged on the bottom surface side of the recess portion, thicknesses or arrangement positions of the heating portions (e.g. heaters) arranged if necessary, or the like. It is to be noted that there is not any special restriction on the thickness of the element base material 31, but the thickness is preferably from 1.5 to three times as much as the depth of the recess portion. Here, "the thickness of the element base material 31" is the thickness of the thickest portion in the above thickness direction.

Moreover, there is not any special restriction on a width of the element base material 31 (i.e. the length of the element base material in a direction which is orthogonal a longitudinal direction and a thickness direction thereof). It is to be noted that the width of the element base material 31 preferably has a size of 1.2 to 2.5 times as much as the width of the recess portion 32 in the width direction of the element base material 31. According to this constitution, a compact particulate matter detection device can be realized.

As to a shape of the element base material 31, as shown in FIG. 1A to FIG. 1D, a sectional shape which is orthogonal to the longitudinal direction may be a rectangular plate-like shape, or the sectional shape may be a semicircular or semi-elliptic rod-like shape (not shown). That is, there is not any special restriction on the shape of the element base material 31, as long as the recess portion 32 can be formed in one surface of the element base material 31.

In the particulate matter detection device 100, there is not any special restriction on the size of the recess portion (i.e. a size of the opening of the recess portion), the depth of the recess portion, and the shape of the opening, as long as the particulate matter collected by the high-voltage dust collection electrode can be collected on the bottom surface side of the recess portion. In addition to the quadrangular shape shown in FIG. 1A (the rectangular shape in FIG. 1A), examples of the shape of the opening can include another polygonal shape, a round shape, and an elliptic shape. The size of the opening or the depth of the recess portion can appropriately be determined in consideration of the intensity of the electric field, a flow rate of the measurement target gas, a flow velocity, or the like.

The element base material 31 is preferably obtained by laminating a plurality of tape-like ceramic materials (ceramic sheets). In consequence, the particulate matter detection device can be prepared by laminating the plurality of tape-like ceramic materials while sandwiching each electrode, each wire or the like between the materials, whereby the particulate matter detection device can efficiently be manufactured.

[2-2] Measurement Electrode:

At least a pair of measurement electrodes are arranged in the bottom surface of the recess portion of the element base material or in the element base material on the bottom surface side of the recess portion, and the measurement electrodes are electrodes for measuring a change of electric characteristics of the bottom surface of the recess portion which is generated by electrically adsorbing the particulate matter on the bottom surface of the recess portion.

There is not any special restriction on the pair of measurement electrodes 12a and 12b for use in the particulate matter detection device 100 of the present embodiment, as long as the pair of electrodes are arranged to face each other via a space. As shown in FIG. 6, the electrodes are combteeth-like electrodes each including a plurality of planarly arranged combteeth portions 13, and a comb spine portion 14 which connects the plurality of combteeth portions 13 of the measurement electrode 12a or 12b to one another at ends thereof, and the combteeth portions 13 of the measurement electrodes 12a and 12b are preferably arranged to engage with each other via a space. According to such a constitution, the effect of the particulate matter detection device of the present embodiment described above is obtained, and additionally the sensitivity of the detection device can further be enhanced. That is, when such combteeth-like electrodes are used, the space between the electrodes can uniformly be narrowed.

There is not any special restriction on thicknesses of the measurement electrodes (the combteeth portions 13 and the comb spine portion 14, when the measurement electrodes are the combteeth-like electrodes), but the thickness is, for example, preferably from 5 μm to 30 μm. Moreover, examples of a material of the measurement electrodes include platinum (Pt), molybdenum (Mo) and tungsten (W).

There is not any special restriction on a width of each of the combteeth portions constituting the measurement electrodes, but the width is, for example, preferably from 30 μm to 400 μm, further preferably from 50 μm to 300 μm, and especially preferably from 80 μm to 250 μm. Moreover, there is not any special restriction on the number of the combteeth portions arranged in each measurement electrode, but the number is, for example, preferably at least 3 or more, further preferably from 3 to 20, and especially preferably from 4 to 8. According to such a constitution, the particulate matter can more accurately be detected.

A space between the combteeth portion of one of adjacent measurement electrodes and the combteeth portion of the other measurement electrode (i.e. a space where the combteeth portions are arranged to engage with each other) is, for example, preferably from 30 μm to 400 μm, further preferably from 50 μm to 300 μm, and especially preferably from 80 μm to 250 μm.

Moreover, when the pair of measurement electrodes are the above combteeth-like electrodes, at least portions of the pair of measurement electrodes where the plurality of combteeth portions engage with each other are arranged in the bottom surface region of the recess portion, and the comb spine portions of the measurement electrodes are further preferably arranged in the wall which forms the recess portion outside the bottom surface region of the recess portion.

When the comb spine portion of at least one of the measurement electrodes is disposed in the wall which forms the recess portion in this manner, the comb spine portion of the measurement electrode is excluded from a substantial detection surface, which enables the satisfactory detection of the particulate matter. When the combteeth-like electrodes are used as described above, the space between combteeth is set to be uniform, and the measurement sensitivity of the detection device can be enhanced. However, a space between portions where the combteeth portions engage with the comb spine portion becomes different from a space between the combteeth portions. Therefore, owing to the comb spine portion (more specifically, the space between the comb spine portion and each combteeth portion), the measurement accuracy of the detection device relatively lowers sometimes.

That is, the comb spine portion of each of the measurement electrodes is disposed in "the wall which forms the recess portion" outside the bottom surface region of the recess portion. According to such a constitution, the comb spine portion which becomes a factor to lower the measurement accuracy is covered with the wall which forms the recess portion, the comb spine portion loses a function of a measurement portion, and hence the comb spine portion does not adversely affect a measured value. In consequence, the particulate matter can more accurately be detected. Moreover, when the comb spine portion is covered in this manner, an initial value of electric characteristics measured by the pair of measurement electrodes (e.g. a value of an electrostatic capacity in a state any particulate matter does not adhere) increases, and hence the present embodiment is remarkably effective, for example, when on-board diagnosis (OBD) of the device is performed by using this initial value.

Moreover, the pair of measurement electrodes 12a and 12b of the particulate matter detection device 100 shown in FIG.

1A to FIG. 7 have measurement electrode lead terminals 17a and 17b (hereinafter referred to as "the lead terminals 17a and 17b" sometimes) in the other end 31b of the element base material 31 via measurement wires 16a and 16b. The measurement electrode lead terminals 17a and 17b are electrically connected to characteristics measurement means (not shown) for measuring the electric characteristics of the pair of measurement electrodes 12a and 12b, and the particulate matter is detected on the basis of the change of the electric characteristics measured by the pair of measurement electrodes 12a and 12b.

It is to be noted that when the lead terminals 17a and 17b of the pair of measurement electrodes 12a and 12b are arranged in the other end 31b of the element base material 31, it is possible to obtain a large space between a portion where the recess portion 32 is disposed (i.e. one end 31a) and the lead terminal 17a or 17b. Therefore, the only one end 31a provided with the recess portion 32 and the like is inserted into a pipe through which a high-temperature exhaust gas passes through, and the other end 31b side provided with the lead terminals 17a and 17b can be projected out of the pipe. When the lead terminals 17a and 17b are set to a high temperature, the detection accuracy of the particulate matter lowers, and stable detection is not easily performed. When the device is used for a long period of time, a contact defect between each electric terminal and a harness connected to the outside is generated, and the measurement cannot be performed sometimes. Therefore, when the lead terminals 17a and 17b are projected from the pipe and are prevented from being exposed to the high temperature, the accurate and stable detection of the particulate matter can be performed.

As shown in FIG. 1B, the lead terminals 17a and 17b arranged in the other end 31b of the element base material 31 are preferably extended in a longitudinal direction along the side surface of the other end 31b of the element base material 31. It is to be noted that in FIG. 1B, the other end 31b of the element base material 31 has a narrowed width, but the width of the other end 31b may be narrowed in this manner or does not have to be narrowed. There is not any special restriction on a shape and a size of the lead terminal 17a or 17b, but each terminal preferably has a strip-like shape with a width of 0.1 to 2.0 mm and a length of 0.5 to 20 mm. Examples of a material of the lead terminals 17a and 17b include nickel (Ni), platinum (Pt), chromium (Cr), tungsten (W), molybdenum (Mo), aluminum (Al), gold (Au), silver (Ag) and copper (Cu).

[2-3] High-Voltage Dust Collection Electrode:

The high-voltage dust collection electrode is embedded in the wall which forms the recess portion of the element base material on the one surface side thereof (the surface side on which the recess portion opens) from the position where the pair of measurement electrodes are arranged, and the electrode is covered with the dielectric material constituting the element base material. When a predetermined voltage (the high voltage) is applied between the high-voltage dust collection electrode 41 and each of the pair of measurement electrodes, the above pair of measurement electrodes become the earths, and the electric field can satisfactorily be generated toward the pair of measurement electrodes 12 (i.e. the bottom surface side of the recess portion 32). It is to be noted that as described later, as the earth for the high-voltage dust collection electrode 41, an earthing electrode (an earth dust collection electrode) may separately be provided in addition to the above pair of measurement electrodes.

There is not any special restriction on a shape of the high-voltage dust collection electrode, as long as the electrode is embedded in the wall which forms the recess portion and the electric field can be generated toward the pair of measurement electrodes 12. Moreover, examples of a material of the high-voltage dust collection electrode include platinum (Pt), molybdenum (Mo), and tungsten (W).

Moreover, there is not any special restriction on a distance from the bottom surface of the recess portion to the high-voltage dust collection electrode in the thickness direction of the element base material, or a distance from the periphery of the recess portion to the high-voltage dust collection electrode as seen from the one surface of the element base material. It is to be noted that from the viewpoint of the intensity of the electric field, the high-voltage dust collection electrode is preferably disposed at a position near the recess portion in a peripheral direction of the recess portion, and is preferably disposed at a position near the upper surface (the one surface) of the recess portion in a thickness direction.

The high-voltage dust collection electrode 41 is connected to a dust collection wire 41b (hereinafter referred to simply as "the wire" sometimes) extending in the longitudinal direction of the element base material 31, and a tip portion (a tip on a side which is not connected to the high-voltage dust collection electrode 41) of the wire 41b is interlayer-connected (via-connected) to a dust collection electrode lead terminal 41a (hereinafter referred to simply as "the lead terminal" sometimes) shown in FIG. 1B. There is not any special restriction on a width of the wire 41b, but the width is, for example, preferably from about 0.2 mm to 1 mm. Moreover, there is not any special restriction on a thickness of the wire 41b, but the thickness is, for example, preferably from about 5 μm to 30 μm. Furthermore, examples of a material of the wire 41b include platinum (Pt), molybdenum (Mo), and tungsten (W). It is to be noted that when the high-voltage dust collection electrodes 41 are arranged away from each other via the recess portion 32 as shown in FIG. 10, the high-voltage dust collection electrodes 41 arranged away from each other can electrically be connected to each other through the above dust collection wire (not shown) on the downside further from the periphery of the recess portion or the bottom surface thereof.

It is to be noted that a lead terminal of the high-voltage dust collection electrode may be disposed in the other end of the element base material (the side opposite to the side provided with the recess portion), but as shown in FIG. 1A to FIG. 1D, the lead terminal 41a of the high-voltage dust collection electrode 41 is preferably disposed at a position between the one end 31a of the element base material 31 and the other end 31b thereof. In consequence, the lead terminal 41a of the high-voltage dust collection electrode 41 and another lead terminal can be arranged via a space. Therefore, when a high voltage is applied to the lead terminal 41a of the high-voltage dust collection electrode 41, surface discharge can effectively be prevented from occurring on the surface of the element base material 31. Examples of a material of the lead terminal 41a include nickel (Ni), platinum (Pt), chromium (Cr), tungsten (W), molybdenum (Mo), aluminum (Al), gold (Au), silver (Ag), copper (Cu), stainless steel, and Kovar.

As conditions of the electric field generated by the high-voltage dust collection electrode, for example, a high-voltage power supply "HJPM-5R0.6 (trade name)" manufactured by Matsusada Precision Inc. can be used. When such a high-voltage power supply is used, for example, a voltage up to 5 kV can be applied.

[2-4] Earth Dust Collection Electrode:

It has been described that in the particulate matter detection device of the present embodiment, when the voltage is applied to the high-voltage dust collection electrode as described above, at least one measurement electrode of the pair of measurement electrodes can be used as an earth.

However, the device may further include an earth dust collection electrode for earthing disposed on the surface of the element base material opposite to the one surface thereof (the surface in which the recess portion opens) from the position where the pair of measurement electrodes are arranged.

Figure 11:
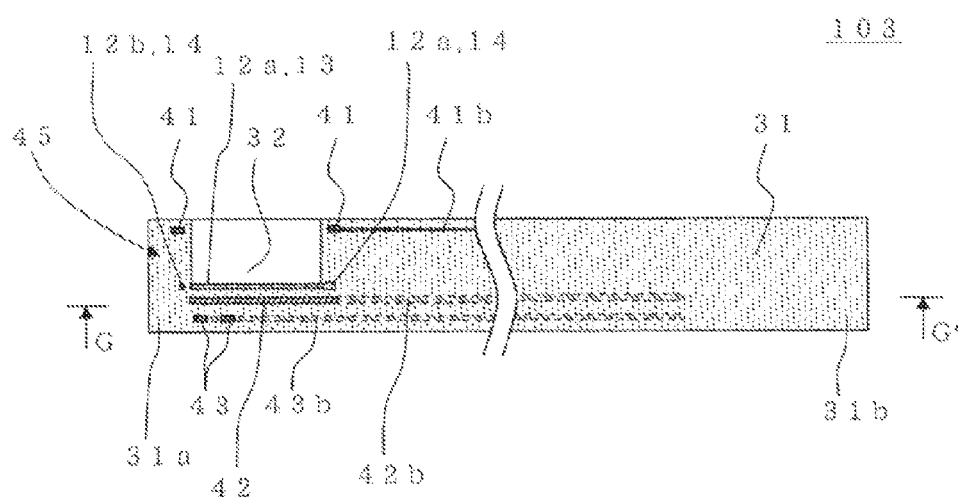
FIG. 11 is a schematic diagram showing a section which is similar to the section cut along the A-A' line of FIG. 1B, in a further embodiment of the particulate matter detection device of the present invention.
Figure 12:
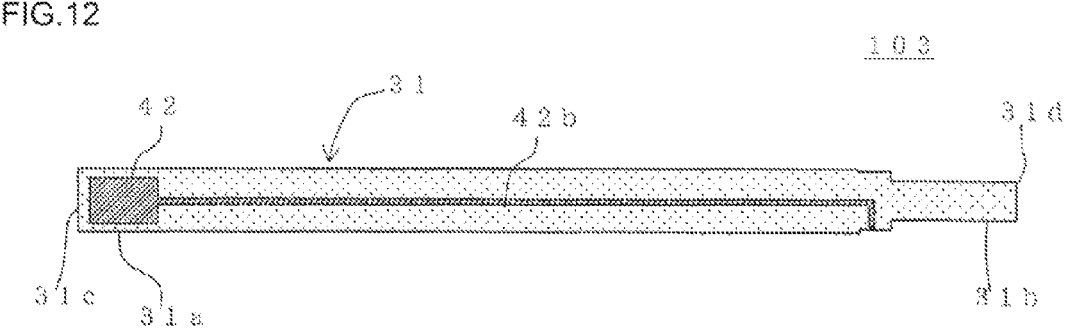
FIG. 12 is a schematic diagram showing a section cut along the G-G' line of FIG. 11.

For example, as a particulate matter detection device 103 shown in FIG. 11 and FIG. 12, the device further includes an earth dust collection electrode 42 for earthing disposed on the surface side of an element base material 31 opposite to the one surface thereof (the surface in which a recess portion 32 opens) from a position where a pair of measurement electrodes 12a and 12b are arranged. In the particulate matter detection device 103, the earth dust collection electrode 92 having about the same size as that of the bottom surface of the recess portion 32 is disposed between the pair of measurement electrodes 12a and 12b and a heating portion 43, and the electrode can perform a function of the earth against the high-voltage dust collection electrode 41, together with the pair of measurement electrodes 12a and 12b.

Here, FIG. 11 is a schematic diagram showing a section which is similar to the section cut along the A-A' line of FIG. 1B, in a further embodiment of the particulate matter detection device of the present invention, and FIG. 12 is a schematic diagram showing a section cut along the G-G' line of FIG. 11.

The earth dust collection electrode 42 is connected to a dust collection wire 42b (hereinafter referred to simply as "the wire" sometimes) extending in a longitudinal direction of the element base material 31, and the wire 42b is connected to a dust collection electrode lead terminal (not shown) in a tip portion thereof (the tip portion on side which is not connected to the earth dust collection electrode 42).

Moreover, examples of a material of the earth dust collection electrode can include platinum (Pt), molybdenum (Mo) and tungsten (W).

The earth dust collection electrode is an electrode for earthing disposed if necessary, and there is not any special restriction on a size of the electrode, but the electrode preferably has such a size that the whole region of the bottom surface of the recess portion can be covered.

[2-5] Characteristics Measurement Means:

The particulate matter detection device of the present embodiment preferably further includes characteristics measurement means for detecting electric characteristics between a pair of measurement electrodes. Specifically, when the electric characteristics to be measured are, for example, an electrostatic capacity, LCR meter 4263B manufactured by Agilent Technologies, or the like can be used. It is to be noted that as the characteristics measurement means, it is possible to use measurement means for use in a heretofore known particulate matter detection device which measures electric characteristics between a pair of electrodes to detect a particulate matter.

The particulate matter detection device 100 shown in FIG. 1A to FIG. 1D has a constitution in which lead terminals of measurement electrodes 12a and 12b are electrically connected to characteristics measurement means (not shown) and electric characteristics of the measurement electrodes 12a and 12b can be detected.

Moreover, in addition to this characteristics measurement means, the particulate matter detection device of the present embodiment may further include particulate matter amount calculation means for calculating an amount of the particulate matter adhering to (attached to) the bottom surface of the recess portion from a change of the electric characteristics obtained by the characteristics measurement means. Examples of the particulate matter amount calculation means can include an integrated circuit which can calculate an amount of the particulate matter by use of a relation between a change amount of the electric characteristics and an amount of the collected particulate matter (e.g. an analytical curve showing the above relation), or the like.

[2-6] Heating Portion:

The particulate matter detection device 100 shown in FIG. 2, FIG. 3 and FIG. 7 includes a heating portion 43 which is disposed (embedded) in an element base material 31 on the bottom surface side of the recess portion 32. When the device is heated by the heating portion 43, the particulate matter collected on the bottom surface of the recess portion 32 can be heated and oxidized (i.e. the device can be regenerated). Moreover, during measurement of a mass of the particulate matter, or the like, an internal space of the recess portion 32 is adjusted at a desirable temperature, and the temperature can be regulated so as to stably measure a change of electric characteristics of the bottom surface of the recess portion 32.

The heating portion 43 may have a wide film-like shape, but as shown in FIG. 7, a linear metal material is preferably disposed in a wave-like shape so that a tip portion thereof is U-turned. According to such a shape, the bottom surface side of the recess portion can uniformly be heated, and the particulate matter adhering to the element base material 31 or a pair of measurement electrodes 12a and 12b (see FIG. 6) can be removed.

In the particulate matter detection device of the present embodiment, the particulate matter to be measured is collected on the bottom surface side of the recess portion by the electric field. Therefore, the heating portion may be disposed only on the bottom surface side of the recess portion so that the bottom surface side of the recess portion can be heated. That is, any heating portion is not required on the opening side of the recess portion. Therefore, as compared with a conventional particulate matter detection device in which a through hole is formed in a device main body, heating portions to be arranged can be decreased, and a constitution of the detection device can be simplified. Moreover, when the heating portions are decreased in this manner, the number of unnecessary wires or the like can be decreased, and the particulate matter can more accurately be detected.

Examples of a material of the heating portion 43 can include platinum (Pt), molybdenum (Mo), and tungsten (W). The heating portion 43 is disposed only in the region of the bottom surface of the recess portion 32 as shown in FIG. 7, but may further be formed to extend to the other end 31b side of the element base material 31. In consequence, there are advantages that a temperature difference between the portion provided with the recess portion and the vicinity of the recess portion can be decreased. Even if rapid heating is performed, the breakdown of the element base material advantageously does not easily occur. The heating portion can preferably raise the temperature in the recess portion up to 650° C.

Moreover, FIG. 7 shows an example where two heating portions 43 are formed by two wires, but there is not any special restriction on the number of the wires which form the heating portion.

Moreover, the heating portions 43 shown in FIG. 7 are connected to heating wires 43b (hereinafter referred to simply as "the wires 43b" sometimes), and the wires 43b are connected to lead terminals 43a (heating portion lead terminals), respectively, as shown in FIG. 1C. The lead terminals 43a of the heating portions 43 are preferably arranged in the other end 31b of the element base material 31 in the same manner as in the lead terminals 17a and 17b of the measurement electrodes 12a and 12b, to avoid the influence of heat when the one end 31a side of the element base material 31 is heated. In FIG. 1C, four lead terminals 43a are arranged side by side in the other side surface of the element base material 31, but the arrangement of the lead terminals 43a is not limited to such arrangement.

[3] Manufacturing Method of Particulate Matter Detection Device:

Next, a method of manufacturing the particulate matter detection device of the present embodiment will be described with respect to an example of a manufacturing method of the particulate matter detection device 100 shown in FIG. 1A to FIG. 1D. It is to be noted that the method of manufacturing the particulate matter detection device is not limited to the following manufacturing method.

[3-1] Preparation of Forming Raw Material:

First, a forming raw material for manufacturing the element base material 31 is prepared. Specifically, at least one ceramic raw material (a dielectric raw material) selected from the group consisting of, for example, alumina, a cordierite forming material, mullite, glass, zirconia, magnesia and titania is mixed with another component for use as the forming raw material, to prepare a slurried forming raw material. As the ceramic raw material (the dielectric raw material), the above raw material is preferable, but the raw material is not limited to this example. As another raw material, a binder, a plasticizer, a dispersant, a dispersion medium or the like is preferably used.

There is not any special restriction on the binder, but an aqueous binder or a nonaqueous binder may be used. As the aqueous binder, methyl cellulose, polyvinyl alcohol, polyethylene oxide or the like can preferably be used, and as the nonaqueous binder, polyvinyl butyral, acrylic resin, polyethylene, polypropylene or the like can preferably be used. Examples of the acrylic resin include (meth)acrylic resin, (meth)acrylic ester copolymer, and acrylic ester-methacrylic ester copolymer.

An amount of the binder to be added is preferably from 3 parts by mass to 20 parts by mass, and further preferably from 6 parts by mass to 17 parts by mass with respect to 100 parts by mass of the dielectric raw material. With such a binder content, when the slurried forming raw material is formed into a green sheet, dried and fired, the generation of cracks or the like can be prevented.

As the plasticizer, glycerin, polyethylene glycol, dibutyl phthalate, di-2-ethyl hexyl phthalate, diisononyl phthalate or the like can be used.

An amount of the plasticizer to be added is preferably from 30 parts by mass to 70 parts by mass, and further preferably from 45 parts by mass to 55 parts by mass with respect to 100 parts by mass of the binder. If the amount is larger than 70 parts by mass, the green sheet becomes excessively soft, and is easily deformed in a step of processing the sheet. If the amount is smaller than 30 parts by mass, the green sheet becomes excessively hard. In this case, when the green sheet is simply bent, the green sheet is cracked, which might deteriorate handling properties.

As an aqueous dispersant, anionic surfactant, wax emulsion, pyridine or the like can be used, and as a nonaqueous dispersant, fatty acid, phosphate ester, synthetic surfactant or the like can be used.

An amount of the dispersant to be added is preferably from 0.5 part by mass to 3 parts by mass, and further preferably from 1 part by mass to 2 parts by mass with respect to 100 parts by mass of the dielectric raw material. If the amount is smaller than 0.5 part by mass, dispersibility of the dielectric raw material might lower, and cracks or the like might be generated in the green sheet. If the amount is larger than 3 parts by mass, the dispersibility of the dielectric raw material does not change, but impurities during firing increase.

As the dispersion medium, water or the like can be used. An amount of the dispersion medium to be added is preferably from 50 parts by mass to 200 parts by mass, and further preferably from 75 parts by mass to 150 parts by mass with respect to 100 parts by mass of the dielectric raw material.

The above raw materials are sufficiently mixed by use of a pot made of alumina and an alumina ball, to prepare a slurried forming raw material for preparing the green sheet. Moreover, these materials are mixed in a ball mill by use of a mono ball, whereby the forming raw material may be prepared.

Next, the obtained slurried forming raw material for preparing the green sheet is stirred and defoamed under a reduced pressure, and further prepared to obtain a predetermined viscosity. The viscosity of the slurried forming raw material obtained in the preparation of the forming raw material is preferably from 2.0 Pa·s to 6.0 Pa·s, further preferably from 3.0 Pa·s to 5.0 Pa·s, and especially preferably from 3.5 Pa·s to 4.5 Pa·s. When a viscosity range is regulated in this manner, the slurry is preferably easily formed into a sheet-like shape. If the slurry viscosity is excessively high or low, it might become difficult to form the sheet. It is to be noted that the viscosity of the slurry is a value measured with a B-type viscosity meter.

[3-2] Forming Processing:

Next, the slurried forming raw material obtained by the above method is formed and processed into a tape-like shape, to prepare a green sheet which is long in one direction. There is not any special restriction on a forming/processing process, as long as the forming raw material can be formed into the sheet-like shape to form the green sheet, and a known process such as a doctor blade process, a press forming process, a rolling process or a calendar rolling process can be used. At this time, two or more green sheets for forming the recess portion are prepared, in which a recess portion forming portion has been hollowed, so that the recess portion is formed when the green sheets are laminated. When a high-voltage dust collection electrode is interposed between such green sheets for forming the recess portion, the high-voltage dust collection electrode can be embedded in the wall which forms the recess portion. It is to be noted that there is not any special restriction on a thickness of the green sheet to be manufactured, but the thickness is preferably from 50 μm to 800 μm.

On the surface of the obtained green sheet, electrodes (a pair of measurement electrodes and the high-voltage dust collection electrode), wires, heating portions, lead terminals and the like are arranged. When the particulate matter detection device 100 shown in FIG. 1A, to FIG. 1D is prepared, as shown in FIG. 2 to FIG. 7, the electrodes, the wires, the heating portions and the lead terminals are preferably printed at corresponding positions of the green sheet so as to arrange the electrodes, the wires, the heating portions and the lead terminals at the predetermined positions. In particular, the high-voltage dust collection electrode is printed around a recess portion in the green sheet forming one recess portion, and embedded in the wall which forms the recess portion, when the green sheets are laminated. Moreover, when the pair of measurement electrodes are formed in a combteeth-like shape, sizes of combteeth portions and comb spine portions and a size of the recess portion are preferably determined so that the comb spine portion of each combteeth-like measurement electrode is hidden behind (covered with) the wall which forms the recess portion of the element base material.

As to a conductive paste for forming (printing) the electrodes, the wires, the heating portions and the lead terminals, in accordance with materials required for forming the electrodes, the wires and the like, a binder and a solvent such as terpineol are added to powder containing at least one selected from the group consisting of gold, silver, platinum, nickel, molybdenum, and tungsten, and sufficiently kneaded by using a tri-roll mill or the like, whereby the paste can be prepared. The conductive paste formed in this manner and containing the materials required for forming the electrodes, the wires and the like is printed on the surface of the green sheet by use of screen printing or the like, to prepare the electrodes, the wires, the heating portions and the lead terminals having predetermined shapes.

Figure 13A:
FIG. 13A is a plan view schematically showing a green sheet for use during the manufacturing of the particulate matter detection device of the present invention.
Figure 13B:
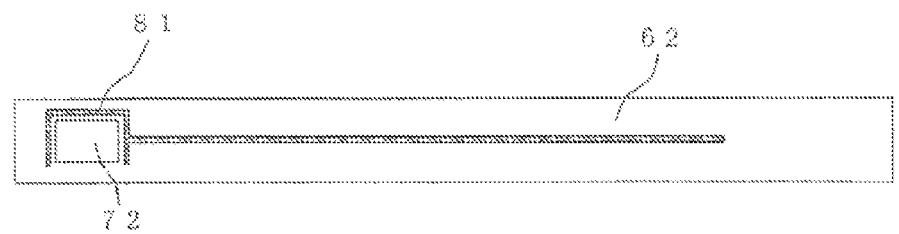
FIG. 13B is a plan view schematically showing the green sheet for use during the manufacturing of the particulate matter detection device of the present invention.
Figure 13C:
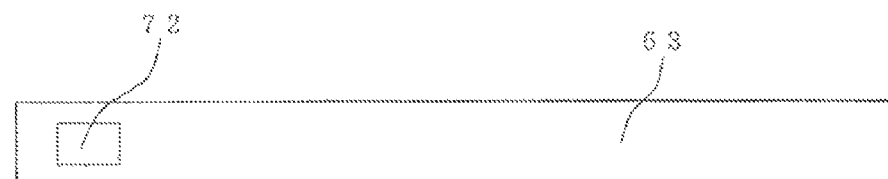
FIG. 13C is a plan view schematically showing the green sheet for use during the manufacturing of the particulate matter detection device of the present invention.

More specifically, a plurality of green sheets are first prepared, and as shown in FIG. 13A to FIG. 13C, a hollow is formed through a position to be provided with a recess portion of an element base material, thereby forming green sheets 61, 62 and 63 for forming the recess portion. As shown in FIG. 13B, a high-voltage dust collection electrode 81 is disposed around a recess portion 72 (a hollowed portion) of the recess portion forming green sheet 62 of these green sheets. Furthermore, a wire is formed as required for the disposed high-voltage dust collection electrode 81, to prepare the green sheet 62 provided with the high-voltage dust collection electrode.

Figure 13D:
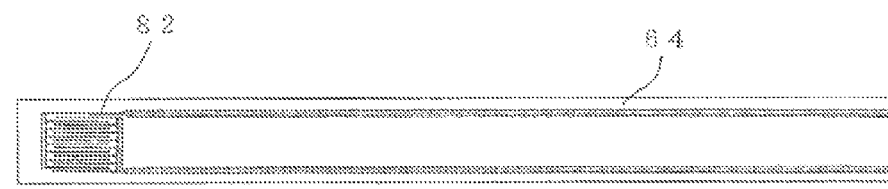
FIG. 13D is a plan view schematically showing the green sheet for use during the manufacturing of the particulate matter detection device of the present invention.

Furthermore, as shown in FIG. 13D, a pair of measurement electrodes 82 are arranged at a position of another green sheet 64 where a bottom portion of a recess portion of the recess portion forming green sheet 63 (see FIG. 13C) is to be formed, to form the green sheet 64 provided with the measurement electrodes. It is to be noted that in this case, there are arranged a pair of measurement wires extending from the measurement electrodes to the other end of the element base material, respectively.

Figure 13E:
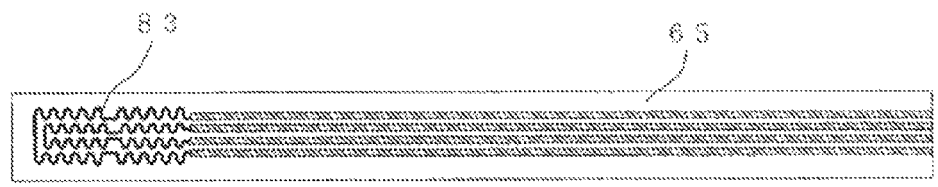
FIG. 13E is a plan view schematically showing the green sheet for use during the manufacturing of the particulate matter detection device of the present invention.

Furthermore, as shown in FIG. 13E, a heating portion 83 is disposed at a position of another green sheet 65 where at least the recess portion 72 (see FIG. 13B) is to be formed, to form the green sheet 65 provided with the heating portion. The green sheet 65 provided with the heating portion is also provided with wires extending toward the other end of a device main body.

Afterward, the green sheets 61 and 63 for forming the recess portion (see FIG. 13A and FIG. 13C), in which another electrode and the like are not arranged, are superimposed on the green sheet 62 provided with high-voltage dust collection electrode (see FIG. 13B), to cover the dust collection electrode and the wires with the green sheets, thereby obtaining the green sheet in which the dust collection electrode is embedded.

Next, the obtained green sheet including an embedded dust collection electrode and still another green sheet (not shown) are laminated so as to sandwich the green sheet 64 provided with the measurement electrodes therebetween (see FIG. 13D). Furthermore, the green sheet 65 provided with the heating portion (see FIG. 13E) is laminated on the outside of the green sheet, to form a green sheet laminate in which the high-voltage dust collection electrode, the pair of measurement electrodes and the heating portion are embedded, respectively. Here, FIG. 13A to 13E are plan views schematically showing the green sheets for use during the manufacturing of the particulate matter detection device of the present invention.

The above plurality of green sheets may simultaneously be laminated, or, for example, the green sheet including the embedded high-voltage dust collection electrode is first prepared and then laminated on another green sheet. The laminating is preferably performed while pressurizing.

In the above manufacturing method of the particulate matter detection device of the present invention, desirable electrodes and the like are arranged on a plurality of green sheets, and the green sheets provided with the electrodes and the like are laminated thereon, dried and fired to manufacture the particulate matter detection device, whereby the particulate matter detection device of the present invention can efficiently be manufactured.

[3-3] Firing:

Next, the green sheet laminate is dried and fired to obtain the particulate matter detection device. Further specifically, the obtained green sheet laminate is dried at 60 to 150° C., and fired at 1200 to 1600° C. to prepare the particulate matter detection device. When the green sheets contain an organic binder, degreasing is preferably performed at 400 to 800° C. before the firing.

EXAMPLES

Hereinafter, the present invention will further specifically be described with respect to examples, but the present invention is not limited to these examples.

Example 1

(Preparation of Forming Raw Material)

As a dielectric raw material, alumina was used, as a binder, polyvinyl butyral was used, as a plasticizer, di-2-ethyl hexyl phthalate was used, as a dispersant, sorbitan tri-oleate was used, and as a dispersion medium, an organic solvent (xylene: butanol=6:4 (mass ratio)) was used. These materials were placed into a pot made of alumina, and mixed, to prepare a slurried forming raw material for preparing a green sheet. Amounts of the raw materials for use were 7 parts by mass of the binder, 3.5 parts by mass of the plasticizer, 1.5 parts by mass of the dispersant and 100 parts by mass of the organic solvent with respect to 100 parts by mass of alumina.

Next, the obtained slurried forming raw material for preparing the green sheet was stirred and defoamed under a reduced pressure, and prepared so as to obtain a viscosity of 4 Pa·s. The viscosity of the slurry was measured with a B-type viscosity meter.

(Forming Processing)

Next, the slurried forming raw material obtained by the above method was formed and processed into a sheet-like shape by use of a doctor blade process. In this case, as shown in FIG. 13A to FIG. 13C, green sheets 61 to 63 for forming a recess portion were also prepared so that when the green sheets were laminated, a recess portion 72 was formed. A thickness of each green sheet was set to 250 μm. Moreover, a size of an opening of the recess portion was set to 2.25×7.20 mm.

On the surface of the obtained green sheet, as shown in FIG. 13A to FIG. 13E, a pair of measurement electrodes 82, a high-voltage dust collection electrode 81, wires and lead terminals were formed. As to a conductive paste for forming the electrodes, the wires and the lead terminals to be arranged, there were added, to platinum powder, 2-ethyl hexanol as a solvent, polyvinyl butyral as a binder, di-2-ethyl hexyl phthalate as a plasticizer, sorbitan trioleate as a dispersant, alumina as a co-base of the green sheet, and glass frit as a sintering aid. The materials were sufficiently kneaded by using a stone mill and a tri-roll mill, to prepare the conductive paste (in terms of a mass ratio, platinum:alumina:glass frit:2-ethyl hexanol: polyvinyl butyral:di-2-ethyl hexyl phthalate:sorbitan trioleate=80:15:5:50:7:3.5:1).

Moreover, as to a conductive paste for forming heating portions, there were added, to tungsten powder, 2-ethyl hexanol as a solvent, polyvinyl butyral as a binder, di-2-ethyl hexyl phthalate as a plasticizer, sorbitan trioleate as a dispersant, alumina as a co-base of the green sheet, and glass frit as a sintering aid. The materials were sufficiently kneaded by using a stone mill and a tri-roll mill, to prepare the conductive paste (in terms of a mass ratio, tungsten:alumina:glass frit:2-ethyl hexanol:polyvinyl butyral:di-2-ethyl hexyl phthalate: sorbitan trioleate=75.5:15:5:50:7:3.5:1).

The electrodes, the wires, the lead terminals and the heating portions were formed through screen printing by use of the pastes obtained by the above processes. In Example 1, the high-voltage dust collection electrode 81 having a width of 400 μm was disposed with the same height as that of the measurement electrodes at a position of the center of a wall which formed the recess portion. Moreover, each of the measurement electrodes was formed so that a plurality of combteeth portions were connected to each other by a comb spine portion at ends thereof. It is to be noted that "the center of the wall which formed the recess portion" was a position between the outer peripheral surface of the element base material and the inner surface of the recess portion (i.e. the position of the center in a thickness direction of the wall).

When the green sheets provided with the electrodes and the like were laminated, the green sheets were pressurized and laminated by using a uniaxial press machine which can heat the green sheets, to obtain an unfired body of the particulate matter detection device including the green sheet laminate.

(Firing)

The obtained green sheet laminate was dried at 120° C., and fired at 1500° C. to prepare the particulate matter detection device.

Figure 14:
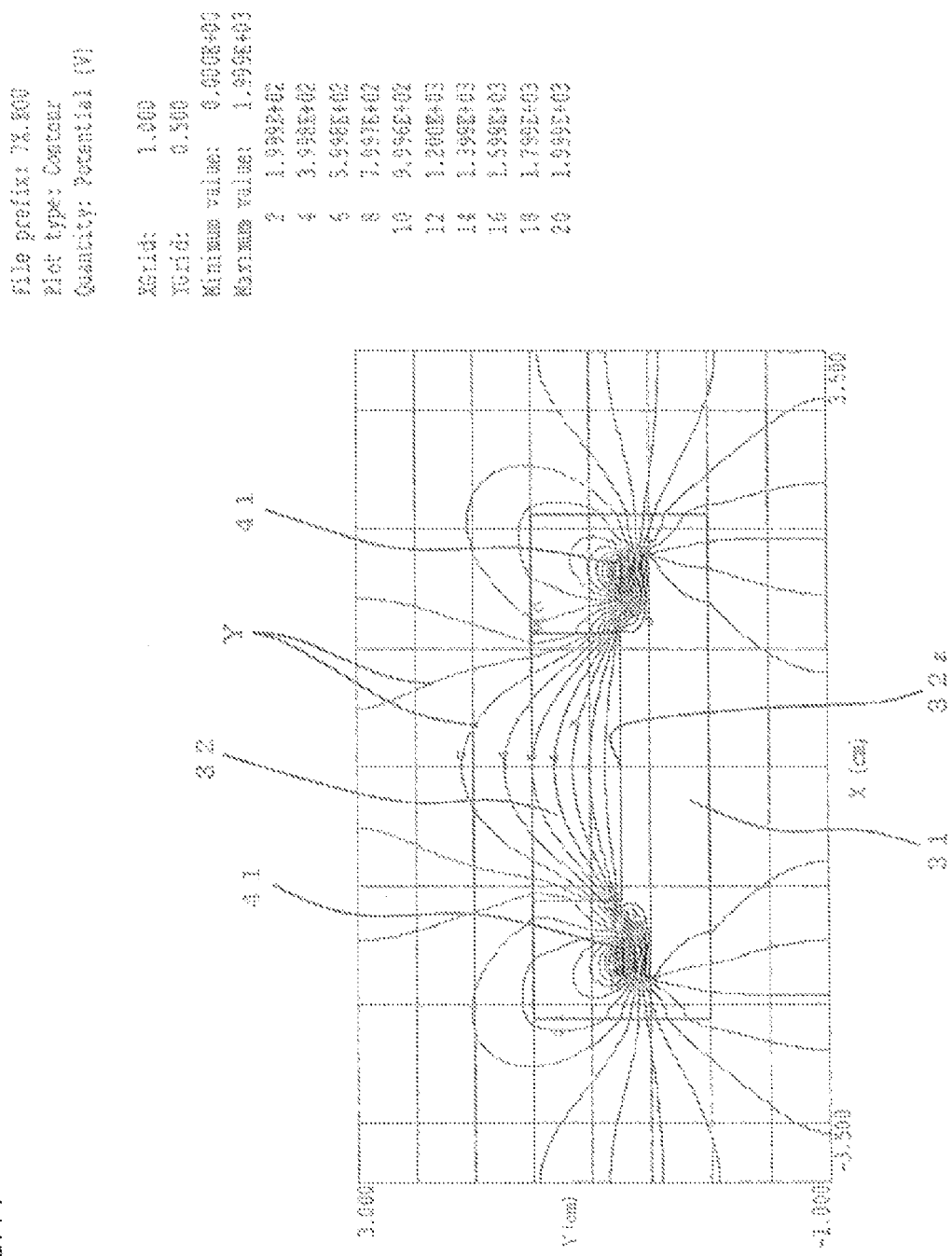
FIG. 14 is an explanatory view schematically showing a state of an electric field generated by a high-voltage dust collection electrode in a particulate matter detection device of Example 1.

A voltage of 2 kV was applied to the high-voltage dust collection electrode of the obtained particulate matter detection device to generate an electric field directed from the high-voltage dust collection electrode to the bottom surface of the recess portion. A state of this electric field is shown in FIG. 14. Here, FIG. 14 is an explanatory view schematically showing the state of the electric field generated by the high-voltage dust collection electrode in the particulate matter detection device of Example 1. It is to be noted that in FIG. 14, a line Y extending from a high-voltage dust collection electrode 41 is an isoelectric line of the electric field, and an electric force line of the electric field is obtained as a line which is orthogonal to this isoelectric line Y.

It is supposed that as shown in FIG. 14, in the particulate matter detection device of Example 1, the electric force line of the electric field generated from the high-voltage dust collection electrode 41 substantially vertically crosses a bottom surface 32*a* of a recess portion 32 formed in an element base material 31 and that a particulate matter included in a measurement target gas flowing along the recess portion 32 follows this electric force line and is satisfactorily collected onto the bottom surface 32*a* of the recess portion 32.

Example 2

Figure 15:
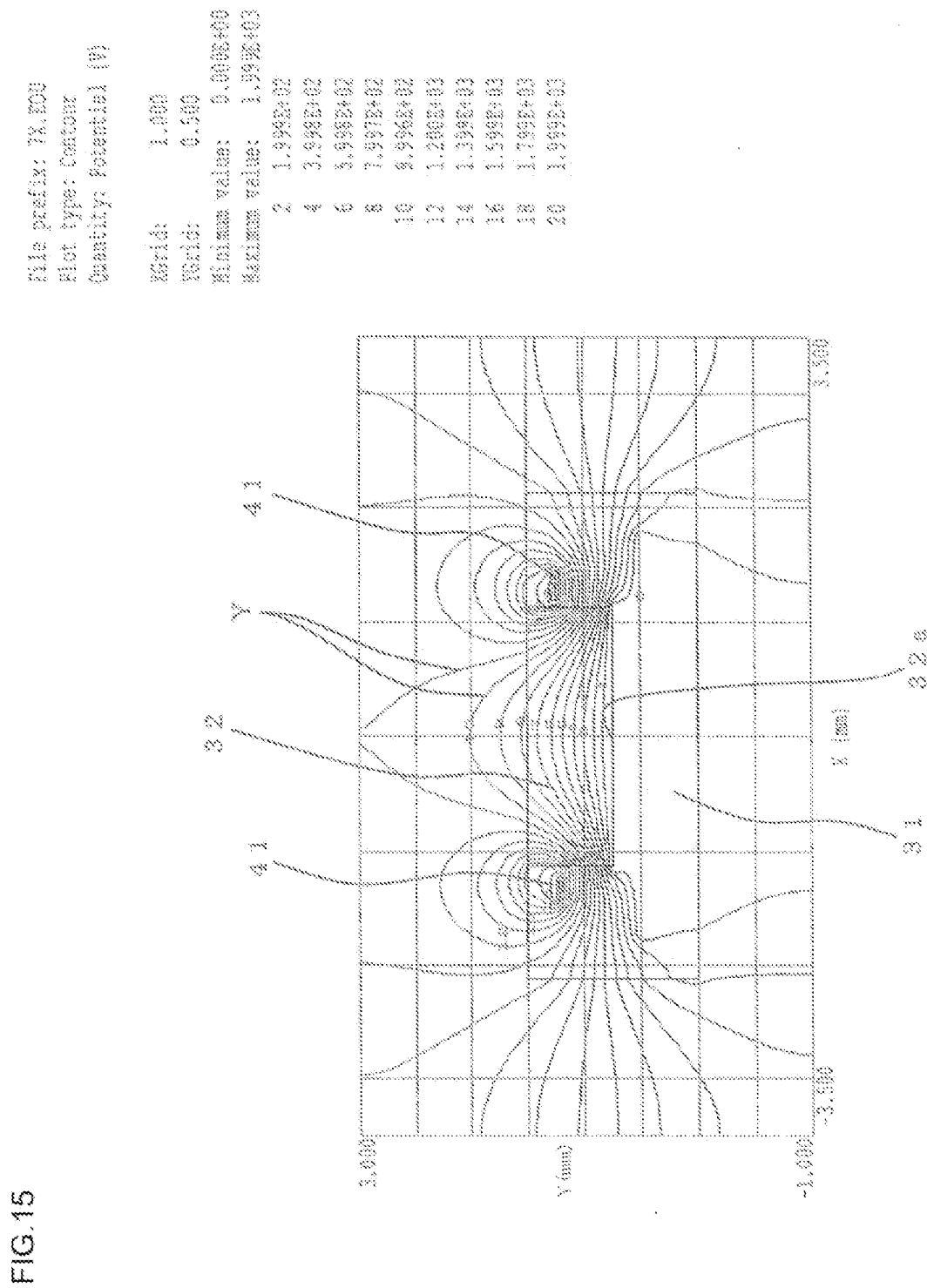
FIG. 15 is an explanatory view schematically showing a state of an electric field generated by a high-voltage dust collection electrode in a particulate matter detection device of Example 2.

In Example 2, a particulate matter detection device was manufactured in the same manner as in Example 1 except that a high-voltage dust collection electrode having a width of 400 μm was disposed closer to an inner periphery of a recess portion peripheral portion (i.e. a wall which formed a recess portion) (i.e. closer to a wall surface of the recess portion, specifically at a position with a distance from the wall surface of the recess portion which was 10 to 30% of a length from the wall surface of the recess portion to the outer peripheral surface of an element base material) at the position which was higher than measurement electrodes. FIG. 15 shows a state of an electric field in a case where a voltage of 2 kV was applied to the high-voltage dust collection electrode of Example 2. Here, FIG. 15 is an explanatory view schematically showing the state of the electric field generated by the high-voltage dust collection electrode in the particulate matter detection device of Example 2.

Example 3

Figure 16:
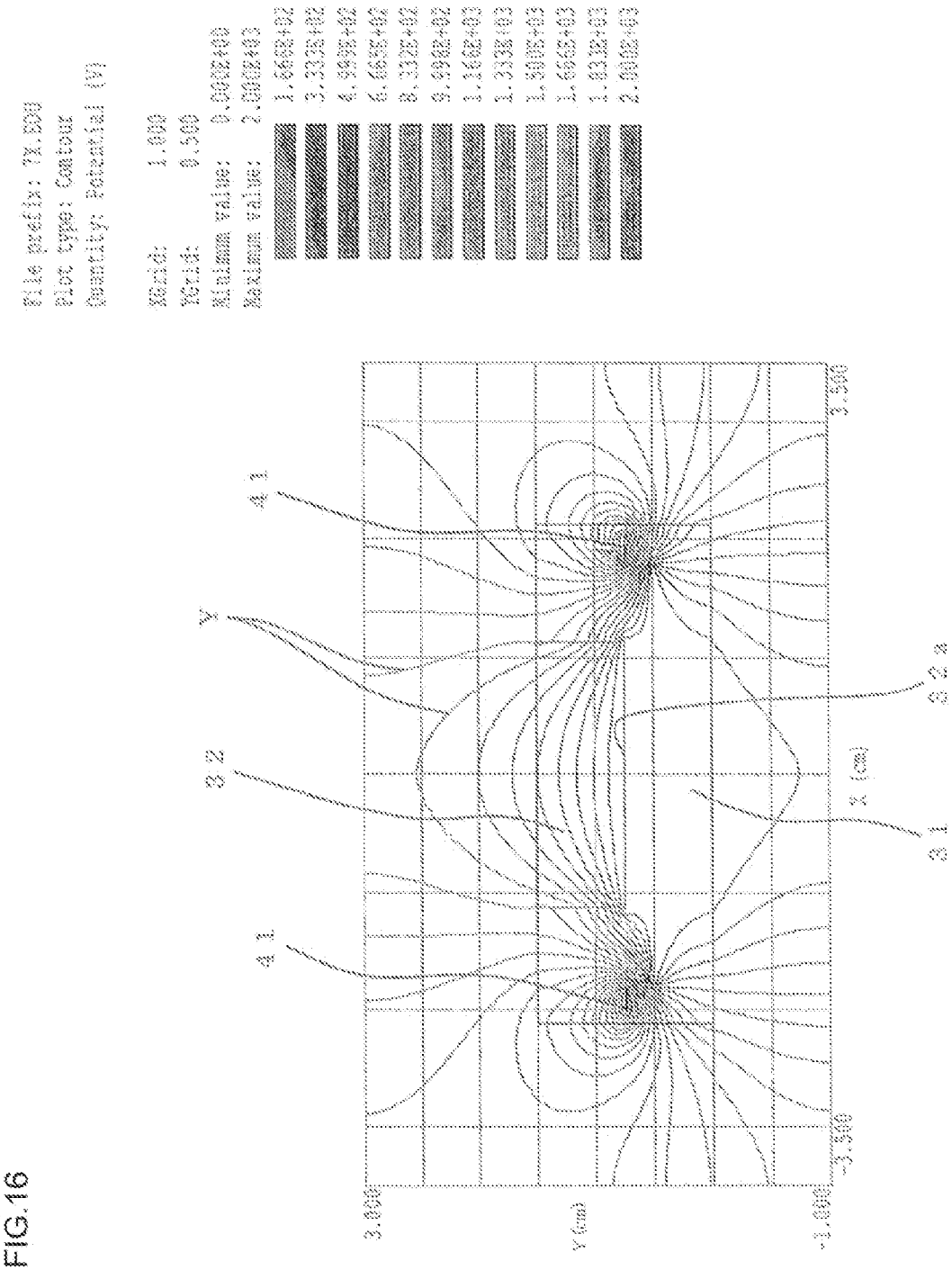
FIG. 16 is an explanatory view schematically showing a state of an electric field generated by a high-voltage dust collection electrode in a particulate matter detection device of Example 3.

In Example 3, a particulate matter detection device was manufactured in the same manner as in Example 1 except that a high-voltage dust collection electrode having a width of 400 μm was disposed closer to an outer periphery of a recess portion peripheral portion (i.e. a wall which formed a recess portion) (i.e. closer to the outer peripheral surface of an element base material, specifically at a position with a distance from a wall surface of the recess portion which was 70 to 90% of a length from the wall surface of the recess portion to the outer peripheral surface of the element base material) at the position having the same height as measurement electrodes. FIG. 16 shows a state of an electric field in a case where a voltage of 2 kV was applied to the high-voltage dust collection electrode of Example 3. Here, FIG. 16 is an explanatory view schematically showing the state of the electric field generated by the high-voltage dust collection electrode in the particulate matter detection device of Example 3.

Example 4

Figure 17:
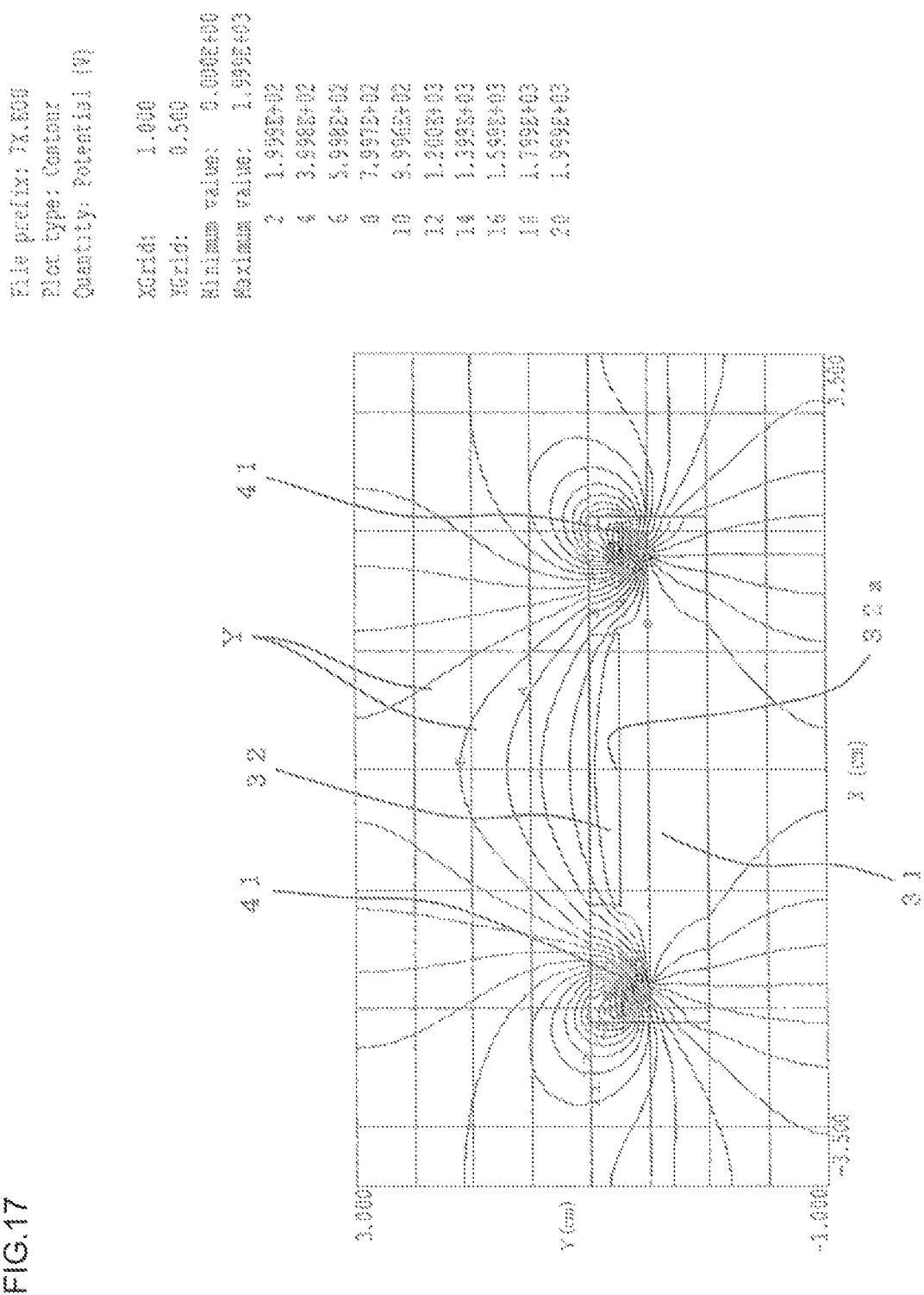
FIG. 17 is an explanatory view schematically showing a state of an electric field generated by a high-voltage dust collection electrode in a particulate matter detection device of Example 4.

In Example 4, a particulate matter detection device was manufactured in the same manner as in Example 1 except that in a shape of a recess portion, a height (a depth) of a peripheral portion (i.e. a wall which formed the recess portion) was set to ⅓ and that a high-voltage dust collection electrode having a width of 400 μm was disposed closer to an outer periphery of the recess portion peripheral portion and at a position having the same height with measurement electrodes. FIG. 17 shows a state of an electric field in a case where a voltage of 2 kV was applied to the high-voltage dust collection electrode of Example 4. Here, FIG. 17 is an explanatory view schematically showing the state of the electric field generated by the high-voltage dust collection electrode in the particulate matter detection device of Example 4.

Example 5

Figure 18:
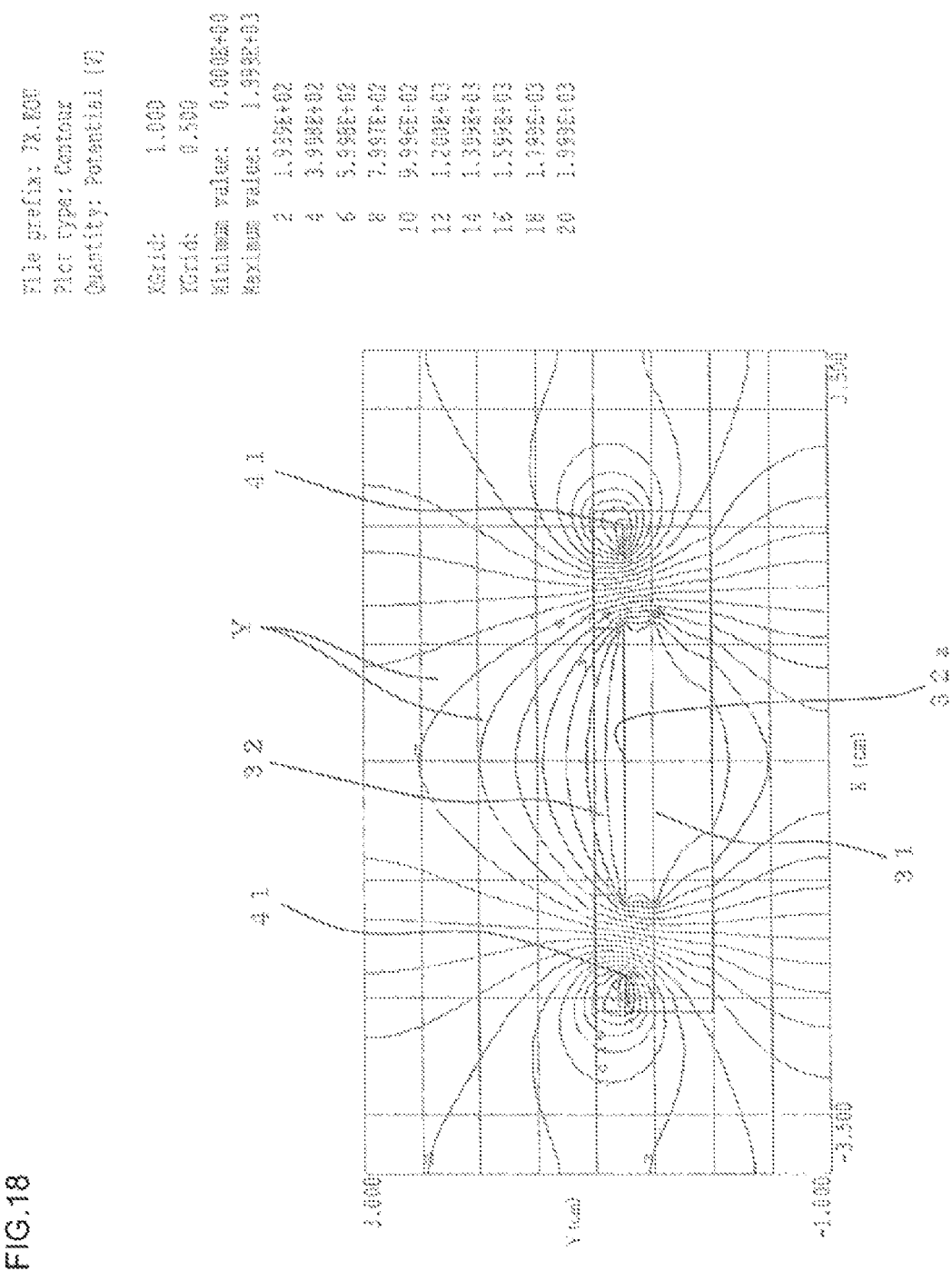
FIG. 18 is an explanatory view schematically showing a state of an electric field generated by a high-voltage dust collection electrode in a particulate matter detection device of Example 5.

In Example 5, a particulate matter detection device was manufactured in the same manner as in Example 4 except that any earth dust collection electrode was not disposed. FIG. 18 shows a state of an electric field in a case where a voltage of 2 kV was applied to a high-voltage dust collection electrode of Example 5. Here, FIG. 18 is an explanatory view schematically showing the state of the electric field generated by the high-voltage dust collection electrode in the particulate matter detection device of Example 5.

Also in the particulate matter detection devices of Examples 2 to 5, it is supposed that the electric force line of the electric field generated from the high-voltage dust collection electrode 41 substantially vertically crosses the bottom surface 32*a* of the recess portion 32 formed in the element base material 31 (i.e. a pair of measurement electrodes) and that the particulate matter included in the measurement target gas flowing along the recess portion 32 follows this electric force line and is satisfactorily collected onto the bottom surface 32*a* of the recess portion 32.

A particulate matter detection device of the present invention can preferably be utilized to immediately detect the generation of a defect of a DPF and to recognize the abnormality of the device, which can contribute to the prevention of air pollution.

Description of Reference Numerals 12, 12a and 12b: measurement electrode, 16a and 16b: measurement wire, 17a and 17b: measurement electrode lead terminal, 31: element base material, 31a: one end, 31b: the other end, 31c: one tip portion, 31d: the other tip portion, 32: recess portion, 32a: bottom surface (the bottom surface of the recess portion), 41: dust collection electrode (high-voltage dust collection electrode), 42: dust collection electrode (earth dust collection electrode), 41a and 42a: dust collection electrode lead terminal, 41b and 42b: dust collection wire, 43: heating portion, 43a: heating portion lead terminal, 43b: heating wire, 45: wall, 52: particulate matter, 61 and 63: green sheet for forming recess portion, 62: green sheet for forming recess portion (green sheet provided with high-voltage dust collection electrode), 64: green sheet for measurement electrode (green sheet provided with measurement electrode), 65: green sheet for heating portion (green sheet provided with heating portion), 72: recess portion, 81: high-voltage dust collection electrode, 82: measurement electrode, 83: heating portion, 100, 101, 102 and 103: particulate matter detection device, X: electric force line, and Y: isoelectric line.

What is claimed is:

1. A particulate matter detection device comprising:
a plate-like element base material including, on one surface thereof, a formed recess portion to collect a particulate matter;
a pair of measurement electrodes arranged in a bottom surface of the recess portion of the element base material or in the element base material on the bottom surface side of the recess portion; and
a high-voltage dust collection electrode embedded in a wall which forms the recess portion of the element base material at the same height position as a position where the pair of measurement electrodes are arranged in a depth direction of the recess portion or on the one surface side position of the element base material from the position where the pair of measurement electrodes are arranged,
wherein an electric field is generated from the high-voltage dust collection electrode to the pair of measurement electrodes arranged in the bottom surface of the recess portion or in the element base material on the bottom surface side of the recess portion, to collect, on the bottom surface side of the recess portion, the particulate matter included in a measurement target gas flowing along the element base material, and a change of electric characteristics between the pair of measurement electrodes is measured to detect the particulate matter collected on the bottom surface side of the recess portion.

2. The particulate matter detection device according to claim 1, wherein the high-voltage dust collection electrode is disposed to surround the periphery of the recess portion excluding a wall thereof positioned on an inflow side of the measurement target gas.

3. The particulate matter detection device according to claim 2, wherein the measurement electrodes constituting the pair of measurement electrodes are combteeth-like electrodes each including a plurality of planarly arranged combteeth portions, and a comb spine portion which connects the plurality of combteeth portions of each of the measurement electrodes to one another at ends thereof, the combteeth portions of the measurement electrodes are arranged to engage with each other via a space, and
the pair of measurement electrodes have a constitution in which at least a portion where the plurality of combteeth portions engage with each other is disposed in a region of the bottom surface of the recess portion and in which the comb spine portion of each of the measurement electrodes is disposed in the wall forming the recess portion outside the bottom surface region of the recess portion.

4. The particulate matter detection device according to claim 3, further comprising:
an earth dust collection electrode for earthing disposed on the surface side of the element base material opposite to the one surface thereof from the position where the pair of measurement electrodes are arranged.

5. The particulate matter detection device according to claim 2, further comprising:
an earth dust collection electrode for earthing disposed on the surface side of the element base material opposite to the one surface thereof from the position where the pair of measurement electrodes are arranged.

6. The particulate matter detection device according to claim 1, wherein the high-voltage dust collection electrode is disposed to surround the whole region around the recess portion.

7. The particulate matter detection device according to claim 6, wherein the measurement electrodes constituting the pair of measurement electrodes are combteeth-like electrodes each including a plurality of planarly arranged combteeth portions, and a comb spine portion which connects the plurality of combteeth portions of each of the measurement electrodes to one another at ends thereof, the combteeth portions of the measurement electrodes are arranged to engage with each other via a space, and
the pair of measurement electrodes have a constitution in which at least a portion where the plurality of combteeth portions engage with each other is disposed in a region of the bottom surface of the recess portion and in which the comb spine portion of each of the measurement electrodes is disposed in the wall forming the recess portion outside the bottom surface region of the recess portion.

8. The particulate matter detection device according to claim 7, further comprising:
an earth dust collection electrode for earthing disposed on the surface side of the element base material opposite to the one surface thereof from the position where the pair of measurement electrodes are arranged.

9. The particulate matter detection device according to claim 6, further comprising:
an earth dust collection electrode for earthing disposed on the surface side of the element base material opposite to the one surface thereof from the position where the pair of measurement electrodes are arranged.

10. The particulate matter detection device according to claim 1, wherein the measurement electrodes constituting the pair of measurement electrodes are combteeth-like electrodes each including a plurality of planarly arranged combteeth portions, and a comb spine portion which connects the plurality of combteeth portions of each of the measurement electrodes to one another at ends thereof, the combteeth portions of the measurement electrodes are arranged to engage with each other via a space, and
the pair of measurement electrodes have a constitution in which at least a portion where the plurality of combteeth portions engage with each other is disposed in a region of the bottom surface of the recess portion and in which the comb spine portion of each of the measurement electrodes is disposed in the wall forming the recess portion outside the bottom surface region of the recess portion.

11. The particulate matter detection device according to claim 10, further comprising:

an earth dust collection electrode for earthing disposed on the surface side of the element base material opposite to the one surface thereof from the position where the pair of measurement electrodes are arranged.

12. The particulate matter detection device according to claim 1, further comprising:

an earth dust collection electrode for earthing disposed on the surface side of the element base material opposite to the one surface thereof from the position where the pair of measurement electrodes are arranged.

\* \* \* \* \*